(12) United States Patent
Beauchamps et al.

(10) Patent No.: US 8,158,635 B2
(45) Date of Patent: Apr. 17, 2012

(54) SOLID FORMS COMPRISING 4-[9-(TETRAHYDRO-FURAN-3-YL)-8-(2,4,6-TRIFLUORO-PHENYLAMINO)-9H-PURIN-2-YLAMINO]-CYCLOHEXAN-1-OL, COMPOSITIONS THEREOF, AND USES THEREWITH

(75) Inventors: Marie G. Beauchamps, Flander, NJ (US); Louise Michelle Cameron, Nazareth, PA (US); Robert Hilgraf, San Diego, CA (US); Mohit Atul Kothare, Bridgewater, NJ (US); Manohar T. Saindane, Monmouth Junction, NJ (US); Jean Xu, Warren, NJ (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 561 days.

(21) Appl. No.: 12/200,146

(22) Filed: Aug. 28, 2008

(65) Prior Publication Data

US 2009/0048275 A1    Feb. 19, 2009

Related U.S. Application Data

(63) Continuation of application No. 11/977,759, filed on Oct. 26, 2007, now abandoned.

(60) Provisional application No. 60/854,757, filed on Oct. 27, 2006.

(51) Int. Cl.
*C07D 473/32* (2006.01)
*A61K 31/52* (2006.01)

(52) U.S. Cl. .................... 514/263.23; 544/277
(58) Field of Classification Search ............ 544/277; 514/263.23
See application file for complete search history.

(56) References Cited

U.S. PATENT DOCUMENTS

| | | | |
|---|---|---|---|
| 7,053,192 B2* | 5/2006 | Li et al. | 536/7.4 |
| 7,256,196 B1 | 8/2007 | Sabat et al. | |
| 7,521,446 B2 | 4/2009 | Albers et al. | |
| 7,723,340 B2 | 5/2010 | Albers et al. | |
| 7,759,342 B2* | 7/2010 | Bennett et al. | 514/234.2 |
| 2005/0135999 A1* | 6/2005 | Elomari et al. | 423/706 |
| 2006/0287344 A1 | 12/2006 | Albers et al. | |
| 2007/0032435 A1* | 2/2007 | Alani et al. | 514/18 |
| 2007/0060598 A1 | 3/2007 | Albers et al. | |
| 2007/0249544 A1* | 10/2007 | Himmelsbach et al. | 514/27 |
| 2008/0004448 A1* | 1/2008 | Wayne et al. | 546/276.7 |
| 2008/0021048 A1 | 1/2008 | Bennett et al. | |
| 2008/0089835 A1* | 4/2008 | Burton | 423/706 |
| 2008/0103186 A1* | 5/2008 | Glover et al. | 514/395 |
| 2008/0139569 A1* | 6/2008 | Rocco et al. | 514/248 |
| 2008/0319024 A1* | 12/2008 | Greil et al. | 514/342 |
| 2009/0069281 A1* | 3/2009 | Austad et al. | 514/183 |
| 2009/0124652 A1* | 5/2009 | Ach et al. | 514/293 |
| 2009/0137794 A1* | 5/2009 | Mendez et al. | 540/78 |
| 2009/0176983 A1* | 7/2009 | Dova et al. | 544/242 |
| 2009/0203705 A1* | 8/2009 | Biagetti et al. | 514/252.02 |
| 2009/0239946 A1* | 9/2009 | McKeown et al. | 514/494 |
| 2009/0275564 A1 | 11/2009 | Albers et al. | |
| 2009/0312320 A1 | 12/2009 | Albers et al. | |
| 2010/0021539 A1* | 1/2010 | Kowalski et al. | 424/464 |

FOREIGN PATENT DOCUMENTS

WO    WO 2006/076595    7/2006
WO    WO 2007/127382    11/2006

OTHER PUBLICATIONS

Chemistry Research Guide—Physical & Chemical Properties <http://www.wcu.edu/library/researchref/resguides/chemistry/Chemistry_PhysicalandChemicalInformation.htm> downloaded from the internet Nov. 22, 2006.*
U.S. Appl. No. 12/779,083, filed May 13, 2010, Bennett et al.
Berge et al., 1977, "Pharmaeutical Salts," J. Pharm. Sciences. Vol;. 66(1):1-19.
Chemburkar et al., 2000, "Dealing withtheimpact of ritonavir polymorphs on thelate stages of bulk drug process development," Organic Process Research & Development, vol. 4:413-417.
Vippagunta et al., 2001, "Crystalline solids," Advanced Drug Delivery, vol. 48:3-26.
Yu, L., 2001, "Amorphoud pharmaceutical solids: preparation, characterization and stabilization," Advanced Drug Delivery, vol. 48:27-42.

* cited by examiner

*Primary Examiner* — Mark Berch
(74) *Attorney, Agent, or Firm* — Jones Day

(57) ABSTRACT

Solid forms comprising 4-[9-(tetrahydro-furan-3-yl)-8-(2,4,6-trifluoro-phenylamino)-9H-purin-2-ylamino]-cyclohexan-1-ol, compositions comprising the solid forms, methods of making the solid forms and methods of their use for the treatment of various diseases and/or disorders are disclosed.

4 Claims, 16 Drawing Sheets

Figure 1:
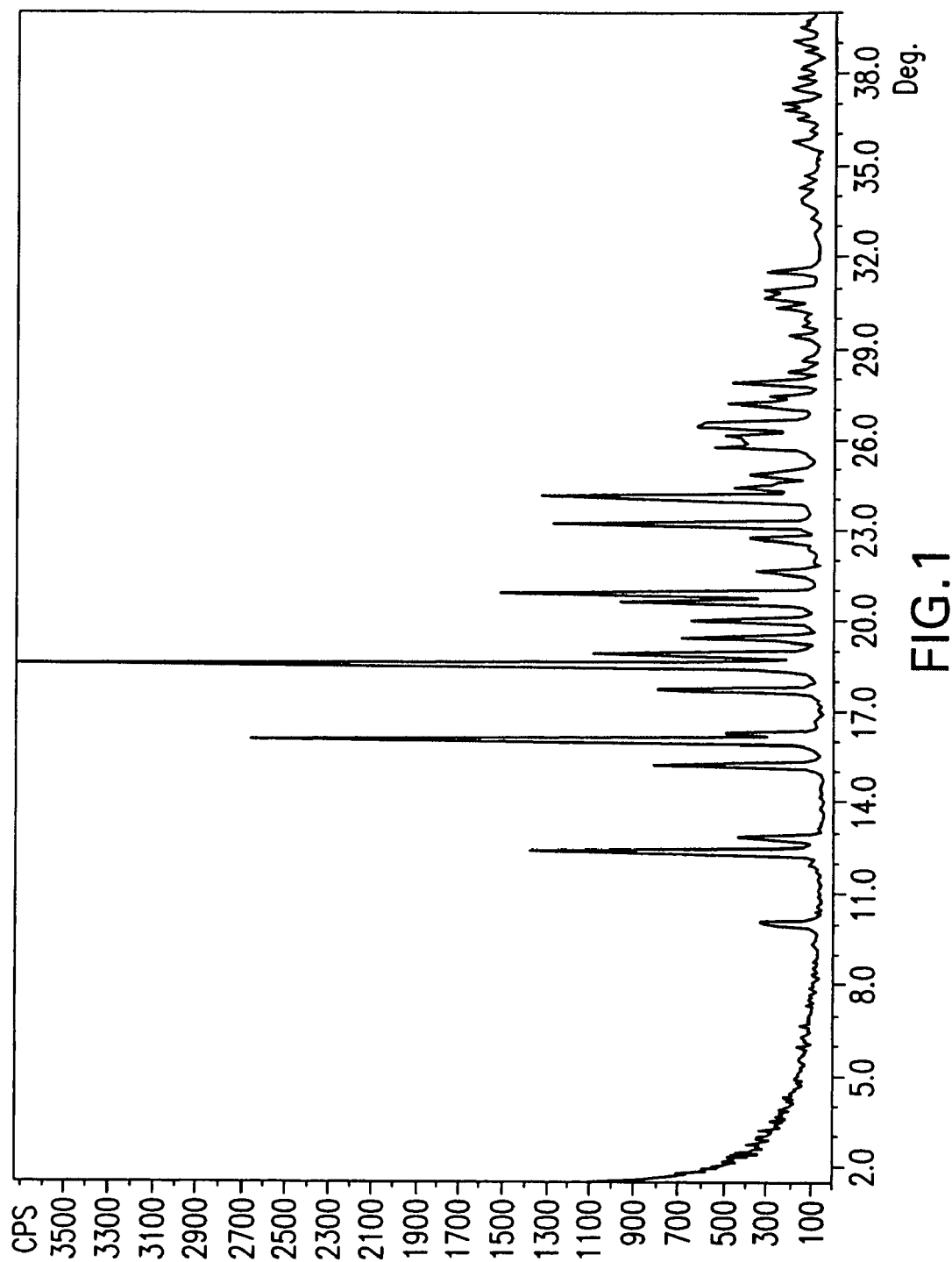

SOLID FORMS COMPRISING 4-[9-(TETRAHYDRO-FURAN-3-YL)-8-(2,4,6-TRIFLUORO-PHENYLAMINO)-9H-PURIN-2-YLAMINO]-CYCLOHEXAN-1-OL, COMPOSITIONS THEREOF, AND USES THEREWITH

This application is a continuation of U.S. application Ser. No. 11/977,759, filed Oct. 26, 2007 now abandoned, which claims the benefit of U.S. Provisional Application No. 60/854,757, filed Oct. 27, 2006, the entire contents of each are incorporated herein by reference.

1. FIELD OF THE INVENTION

Provided herein are solid forms comprising 4-[9-(tetrahydro-furan-3-yl)-8-(2,4,6-trifluoro-phenylamino)-9H-purin-2-ylamino]-cyclohexan-1-ol, compositions comprising the solid forms, methods of making the solid forms and methods of their use for the treatment of various diseases and/or disorders.

2. BACKGROUND OF THE INVENTION

The identification and selection of a solid form of a pharmaceutical compound is complex, given that a change in solid form may affect a variety of physical and chemical properties, which may provide benefits or drawbacks in processing, formulation, stability and bioavailability, among other important pharmaceutical characteristics. Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Dr g. Deliv. Rev.*, (2001) 48:3-26; L. Yu, *Adv. Drug. Deliv. Rev.*, (2001) 48:27-42).

Whether crystalline or amorphous, potential solid forms of a pharmaceutical compound include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette). The importance of discovering polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Additional diversity among the potential solid forms of a pharmaceutical compound may arise from the possibility of multiple-component solids. Crystalline solids comprising two or more ionic species are termed salts (see, e.g., *Handbook of Pharmaceutical Salts: Properties, Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., *Solid State Chemistry of Drugs*, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

The compound chemically named 4-[9-(tetrahydro-furan-3-yl)-8-(2,4,6-trifluoro-phenylamino)-9H-purin-2-ylamino]-cyclohexan-1-ol was disclosed in U.S. patent application Ser. No. 11/332,617, filed Jan. 12, 2006, and International Pub. No. WO 2006/076595, the entireties of each of which is incorporated by reference herein. We have discovered multiple solid forms of 4-[9-(tetrahydro-furan-3-yl)-8-(2,4,6-trifluoro-phenylamino)-9H-purin-2-ylamino]-cyclohexan-1-ol ("Compound I"), and have found that not all of the solid forms of Compound I are equally useful, as assessed by their physical and chemical properties. Thus, certain embodiments herein address the need for improved solid forms of Compound I for, e.g., purity, stability, manufacture, efficacy and bioavailability.

3. SUMMARY OF THE INVENTION

Provided herein are solid forms comprising 4-[9-(tetrahydro-furan-3-yl)-8-(2,4,6-trifluoro-phenylamino)-9H-purin-2-ylamino]-cyclohexan-1-ol ("Compound I"), having particular utility for the treatment, prevention or management of conditions and disorders including, but not limited to, cancer, a cardiovascular disease, a renal disease, an autoimmune condition, an inflammatory condition, macular degeneration, ischemia-reperfusion injury, pain and related syndromes, disease-related wasting, an asbestos-related condition, pulmonary hypertension, central nervous system (CNS) injury/damage or a condition treatable or preventable by inhibition of a kinase pathway.

In certain embodiments, the solid forms are single-component crystal forms of the free base of Compound I. In other embodiments, the solid forms are multiple-component crystal forms, including, but not limited to, salts, co-crystals, solvates, hydrates and/or clathrates of Compound I. In other embodiments, the solid forms are single-component amorphous forms of the free base of Compound I. In other embodiments, the solid forms are multiple-component amorphous forms, including, but not limited to, salts of Compound I. Without intending to be limited by any particular theory, the storage stability, compressibility, bulk density or dissolution properties of the solid forms are believed to be beneficial for manufacturing, formulation and bioavailability of Compound I. Also provided herein are pharmaceutical compositions comprising the solid forms and methods of their use for the treatment, prevention or management of conditions and disorders including, but not limited to, cancer, a cardiovascular disease, a renal disease, an autoimmune condition, an inflammatory condition, macular degeneration, ischemia-reperfusion injury, pain and related syndromes, disease-related wasting, an asbestos-related condition, pulmonary hypertension, central nervous system (CNS) injury/damage or a condition treatable or preventable by inhibition of a kinase pathway.

The solid forms are formed from Compound I, which is described in U.S. patent application Ser. No. 11/332,617, filed Jan. 12, 2006, and International Pub. No. WO 2006/076595, the entireties of each of which is incorporated by reference herein.

Compound I has the following structure (I):

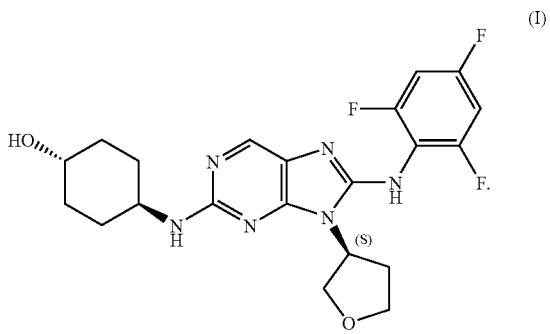

Also provided herein are pharmaceutical compositions comprising a single-component crystal form, a multiple-component crystal form, a single-component amorphous form and/or a multiple-component amorphous form of Compound I and a pharmaceutically acceptable diluent, excipient or carrier.

Also provided herein are methods for the treatment, prevention or management of conditions or disorders including, but not limited to, cancer, a cardiovascular disease, a renal disease, an autoimmune condition, an inflammatory condition, macular degeneration, ischemia-reperfusion injury, pain and related syndromes, disease-related wasting, an asbestos-related condition, pulmonary hypertension, central nervous system (CNS) injury/damage or a condition treatable or preventable by inhibition of a kinase pathway, wherein such methods comprise administering to a subject, e.g., a human, in need of such treatment, prevention or management a therapeutically and prophylactically effective amount of a solid form provided herein.

Further embodiments herein provide methods of making, isolating and/or characterizing the solid forms of the invention.

Certain solid forms provided herein are useful as active pharmaceutical ingredients for the preparation of formulations for use in animals or humans. Thus, certain embodiments provided herein encompass the use of these solid forms as a final drug product. Certain solid forms and final drug products provided herein are useful, for example, for the treatment, prevention or management of the conditions and disorders listed above.

4. BRIEF DESCRIPTION OF THE DRAWINGS

FIG. 1 provides a representative X-ray powder diffraction (XRPD) pattern of Form A of the free base of Compound I.

Figure 2:
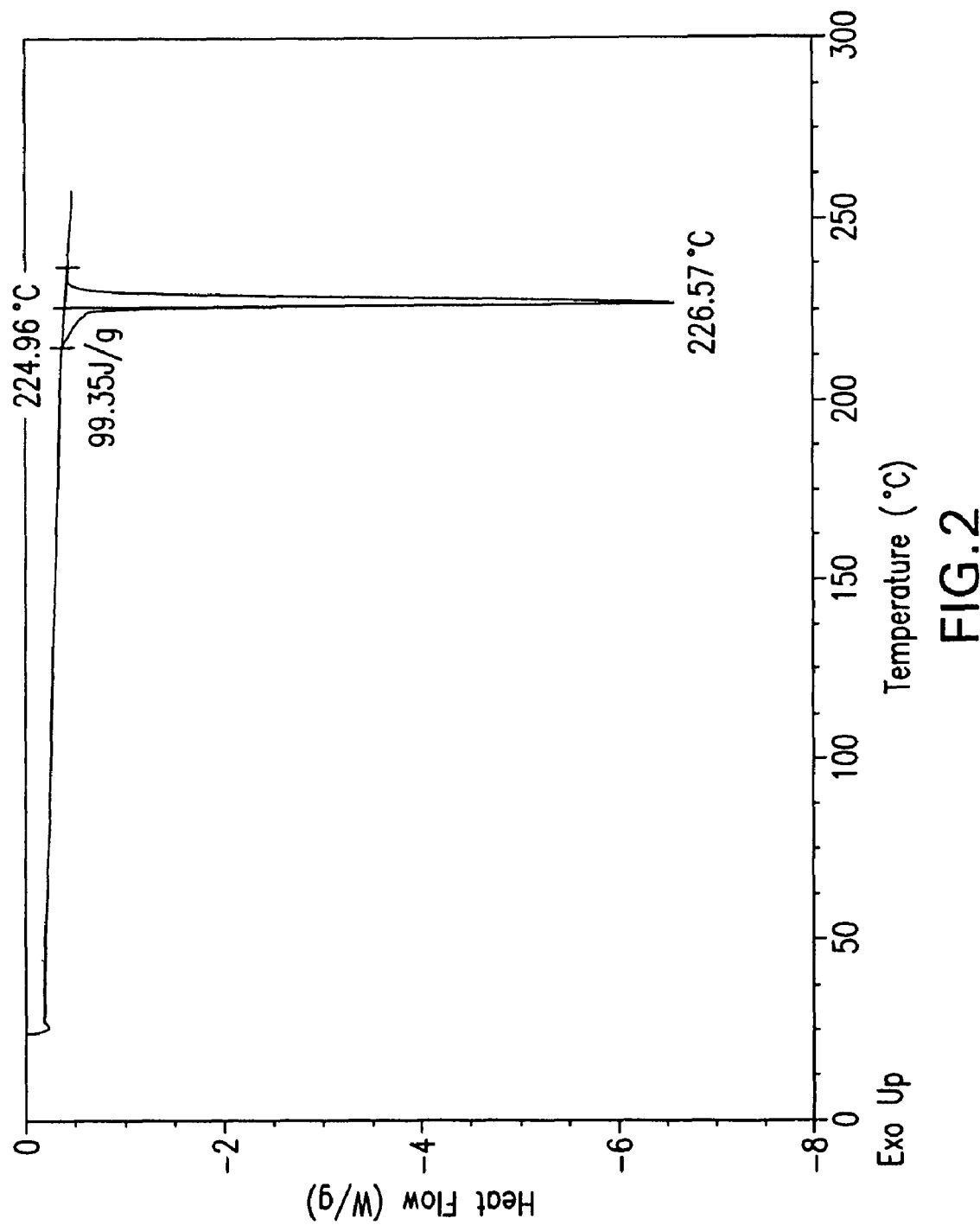

FIG. 2 provides a representative differential scanning calorimetry (DSC) thermogram of Form A of the free base of Compound I.

Figure 3:
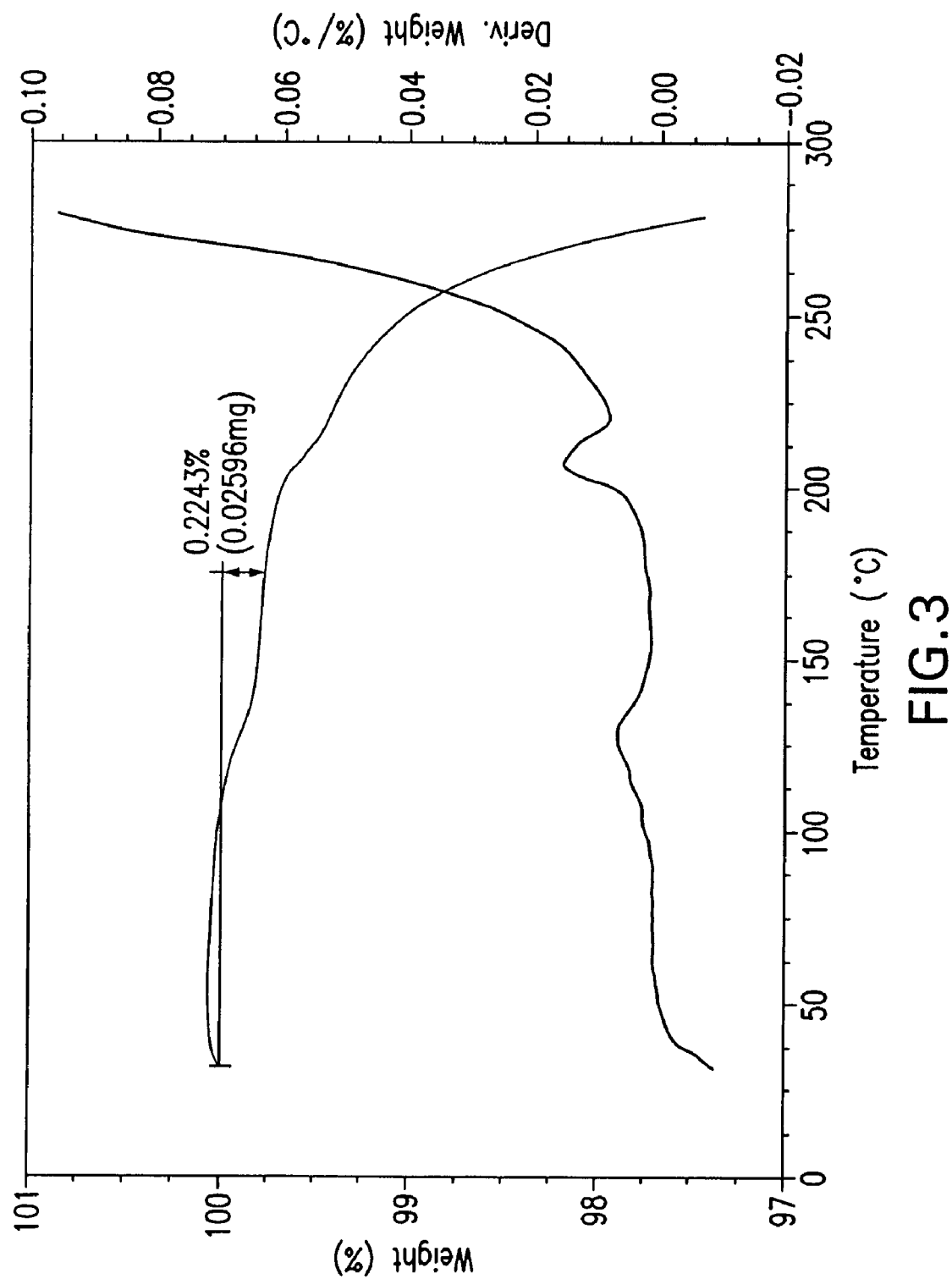

FIG. 3 provides a representative thermal gravimetric analysis (TGA) thermogram of Form A of the free base of Compound I.

Figure 4:
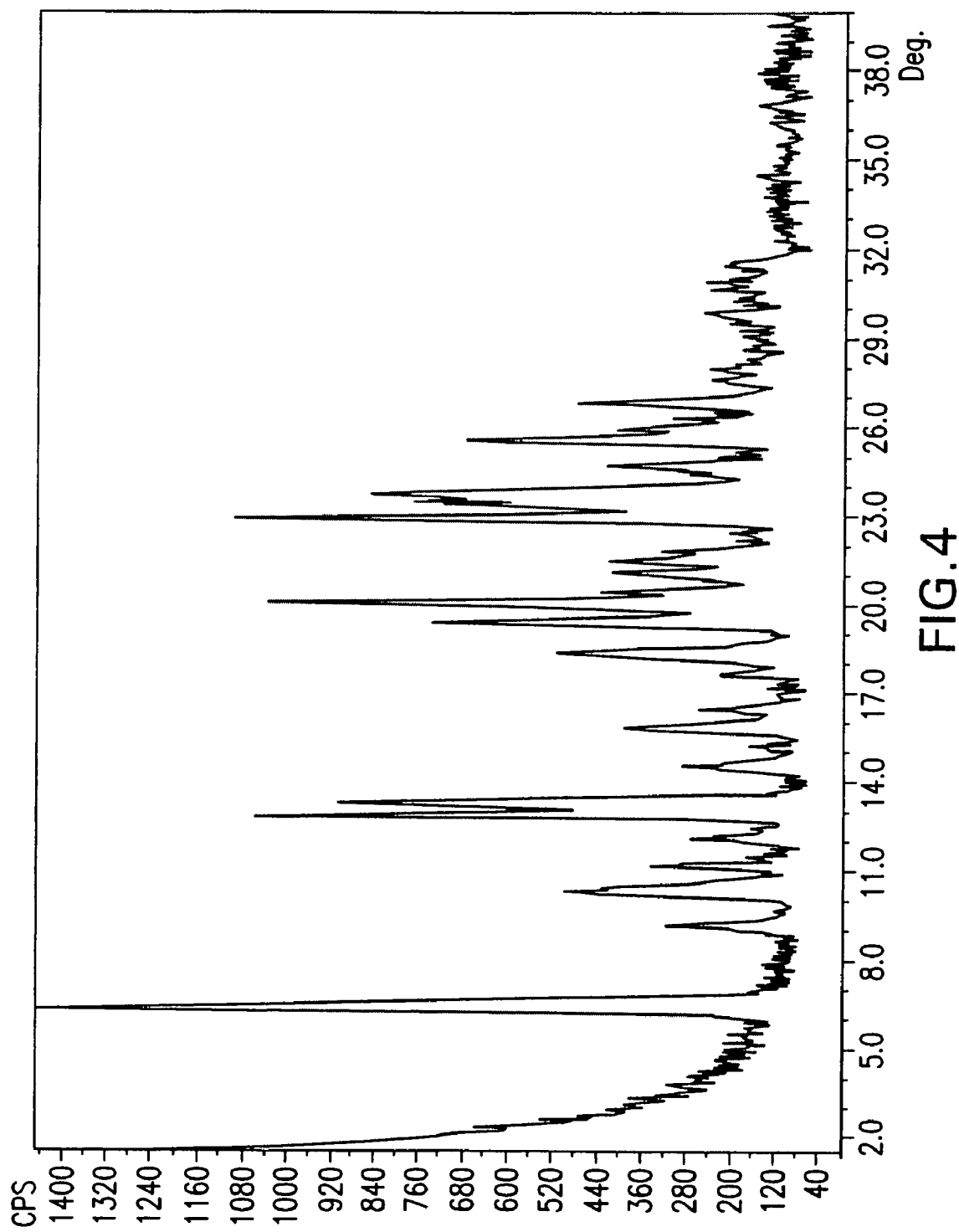

FIG. 4 provides a representative XRPD pattern of a hydrate crystal form of the free base of Compound I.

Figure 5:
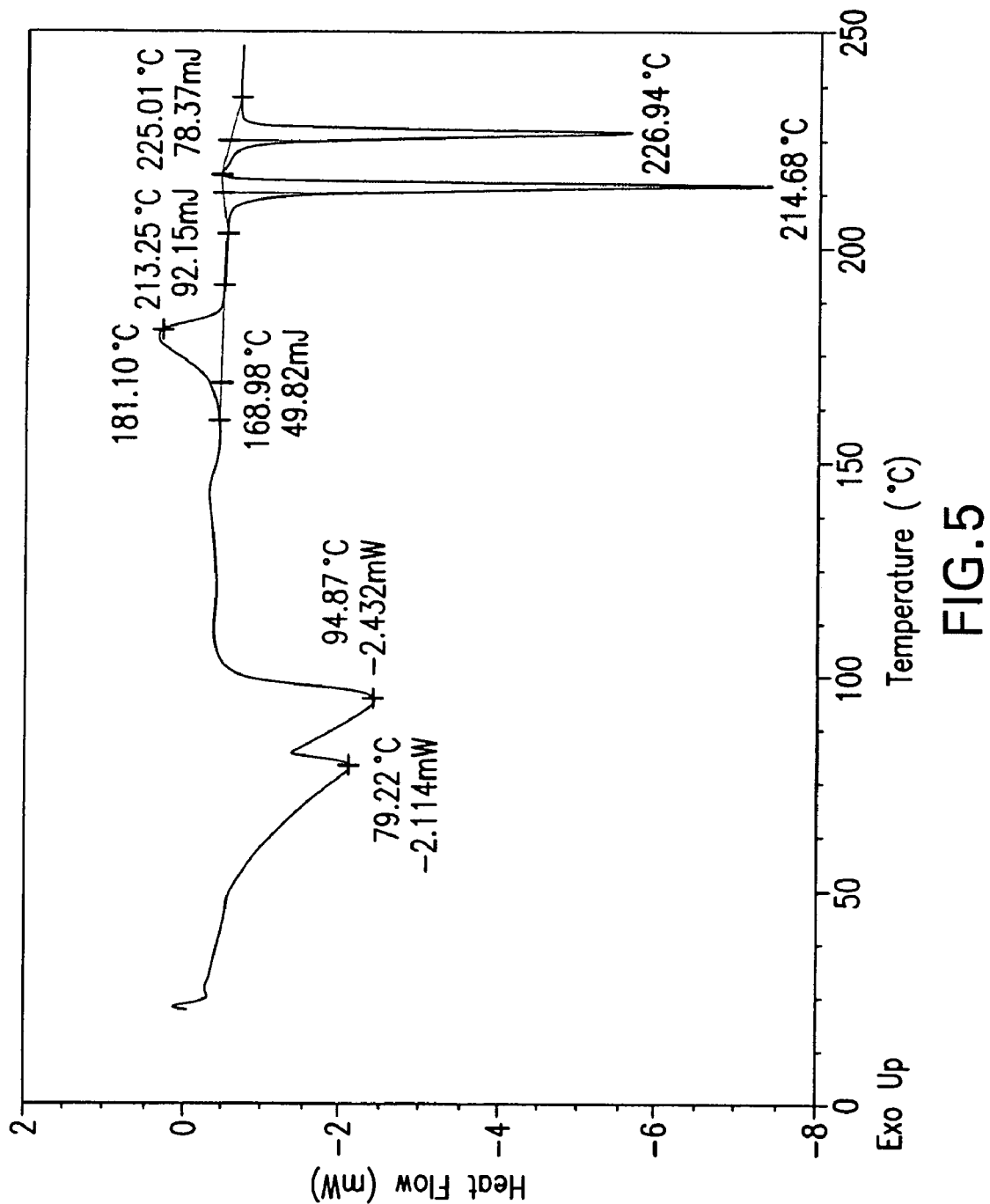

FIG. 5 provides a representative DSC thermogram of a hydrate crystal form of the free base of Compound I.

Figure 6:
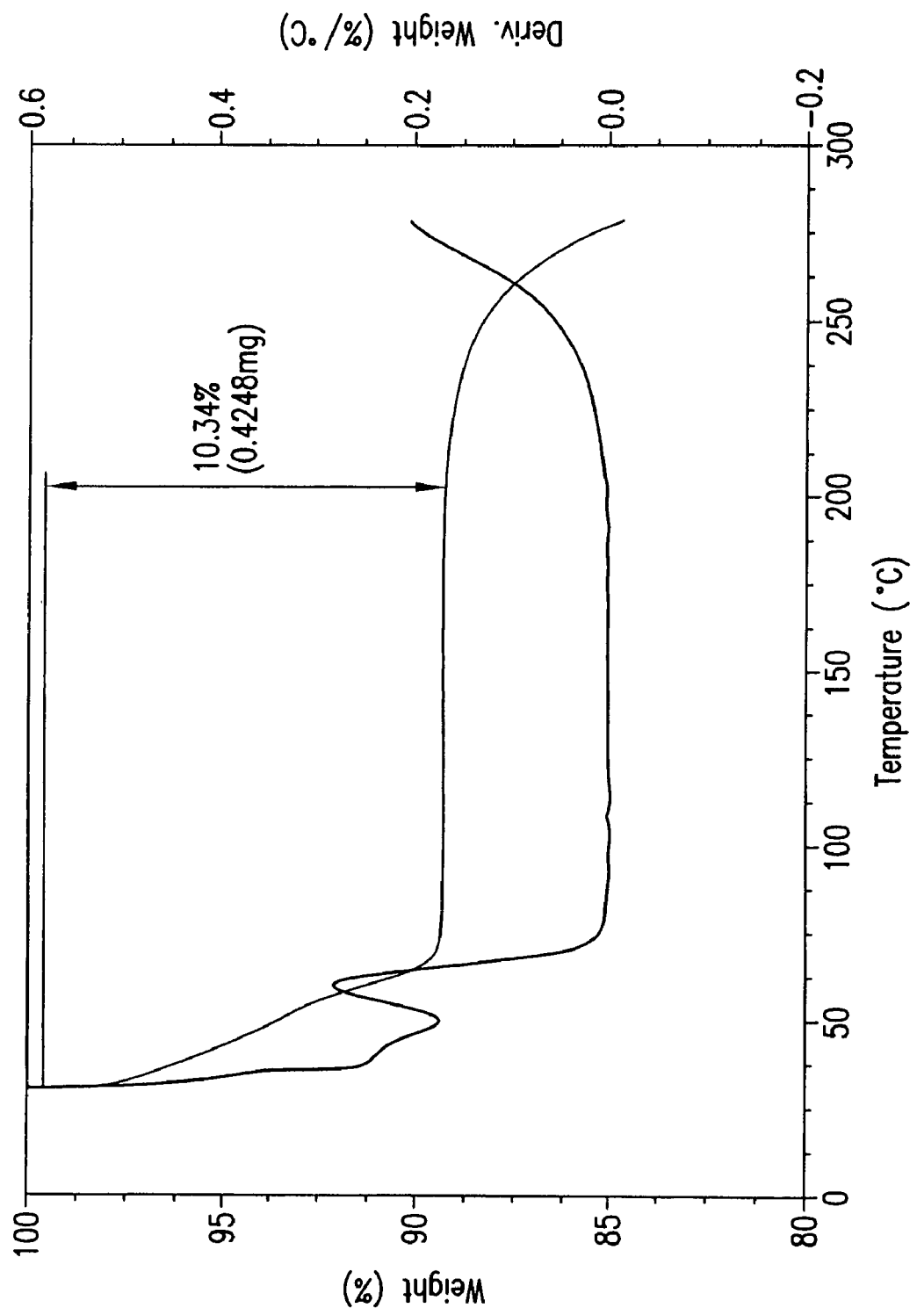

FIG. 6 provides a representative TGA thermogram of a hydrate crystal form of the free base of Compound I.

Figure 7:
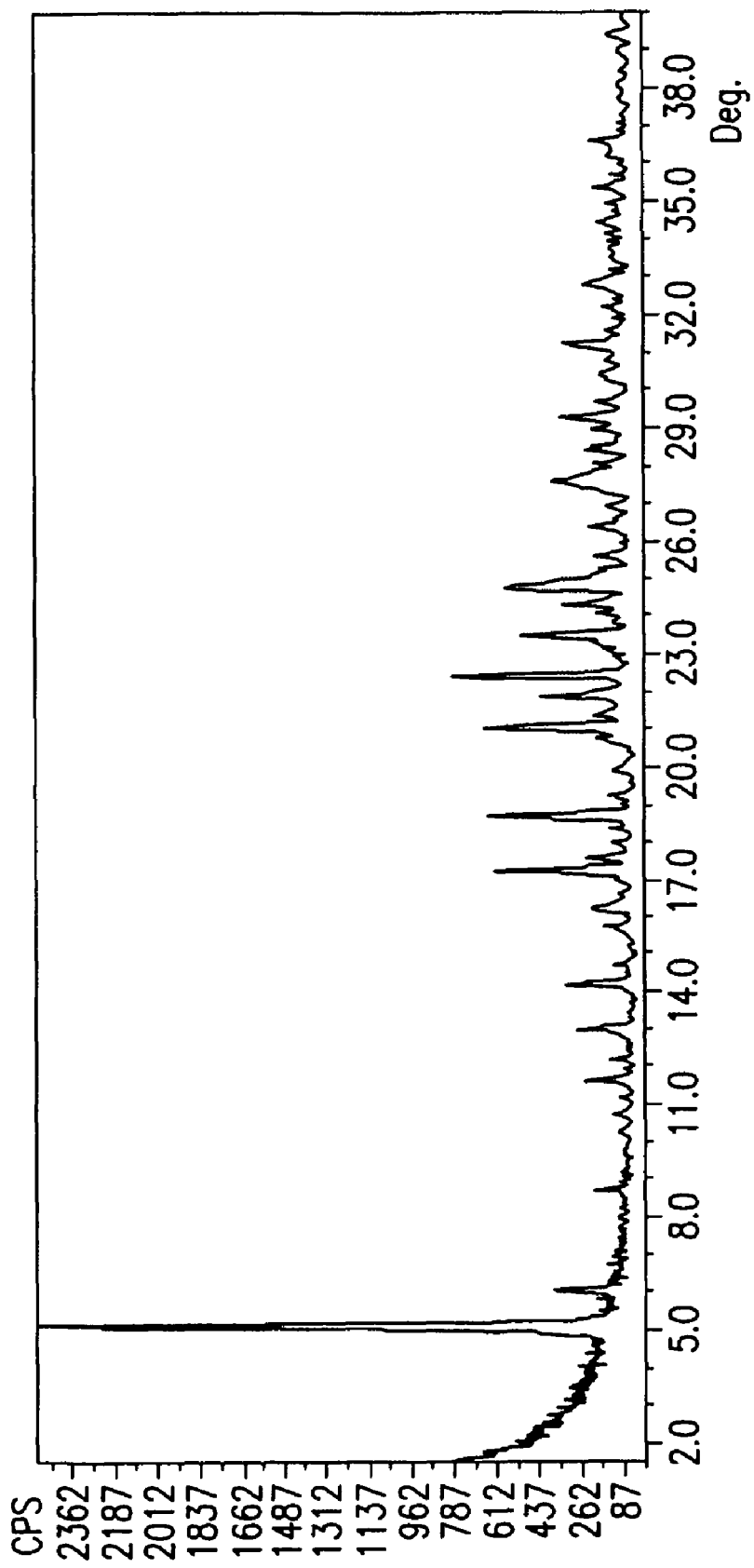
Figure 8:
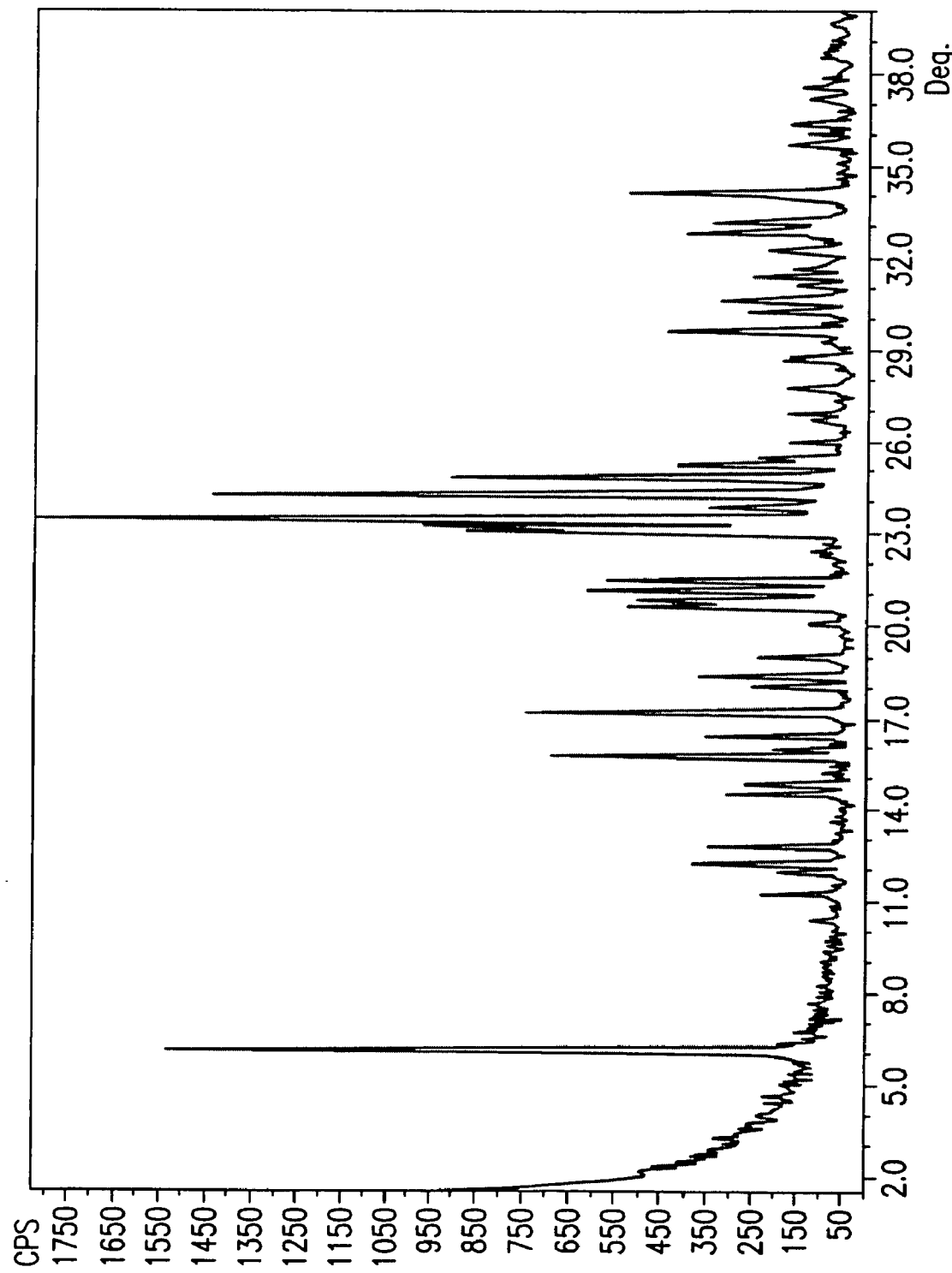

FIG. 7 and FIG. 8 provide representative XRPD patterns of Form A of the hydrochloride salt of Compound I.

Figure 9:
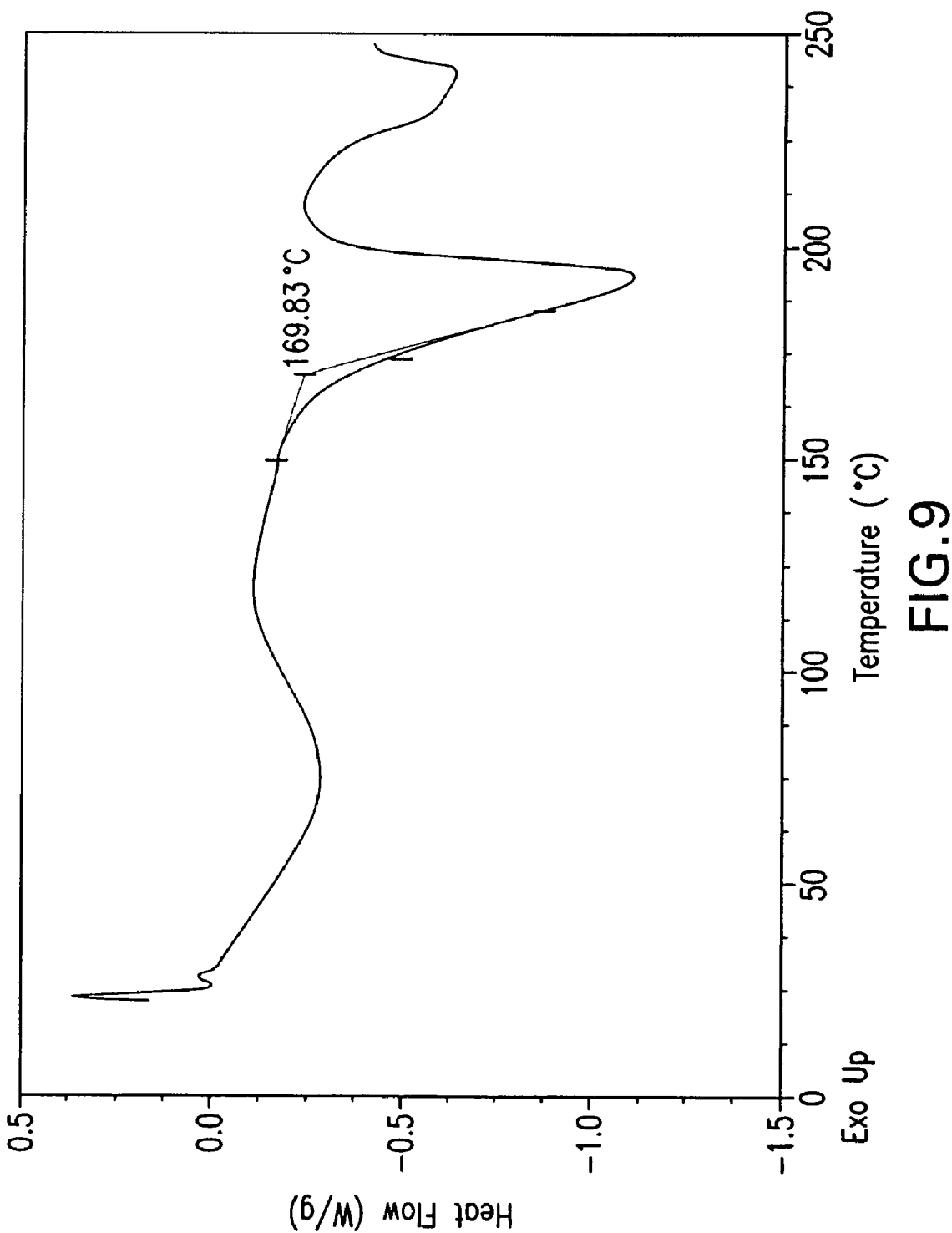

FIG. 9 provides a representative DSC thermogram of Form A of the hydrochloride salt of Compound I.

Figure 10:
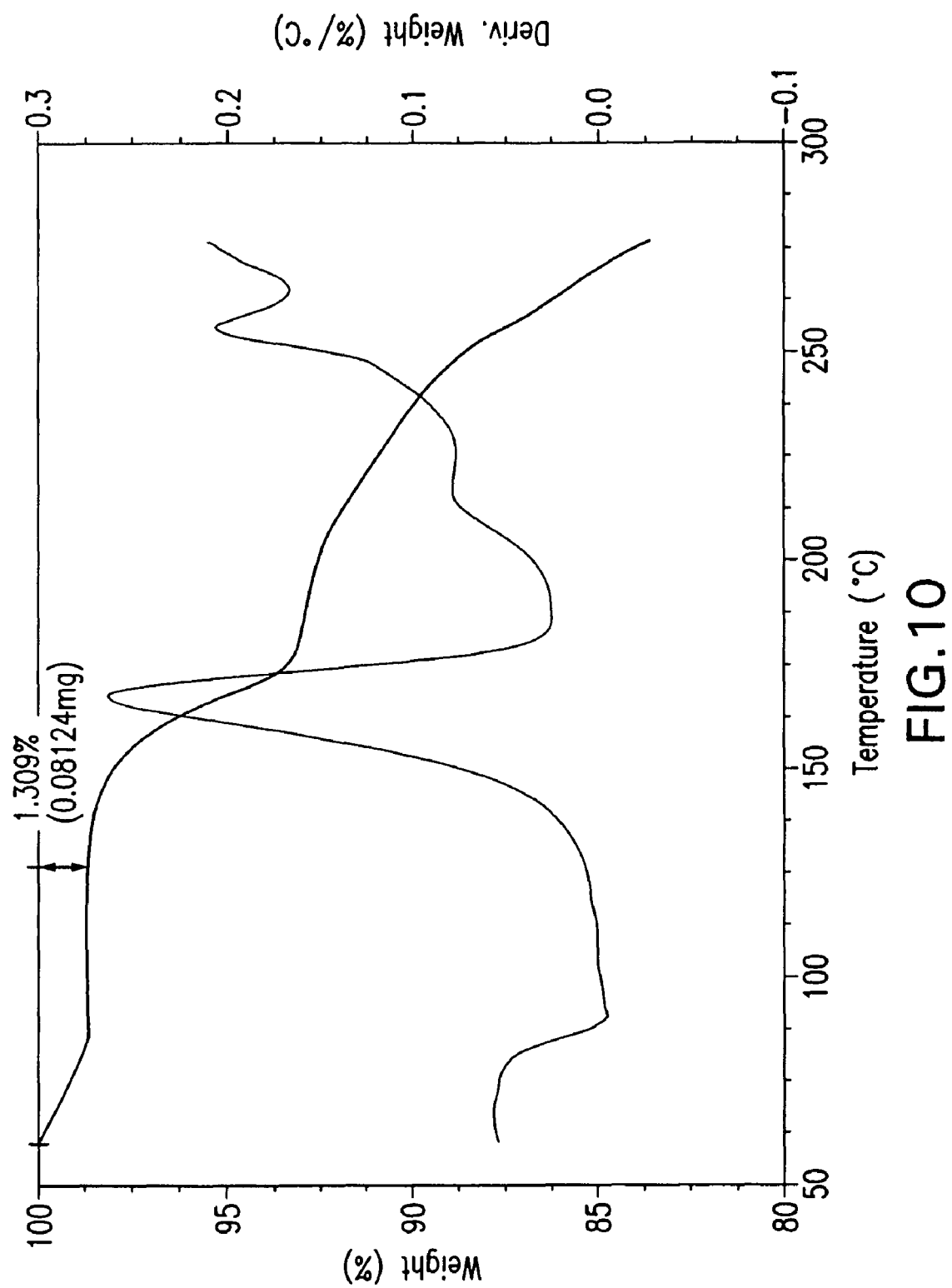

FIG. 10 provides a representative TGA thermogram of Form A of the hydrochloride salt of Compound I.

Figure 11:
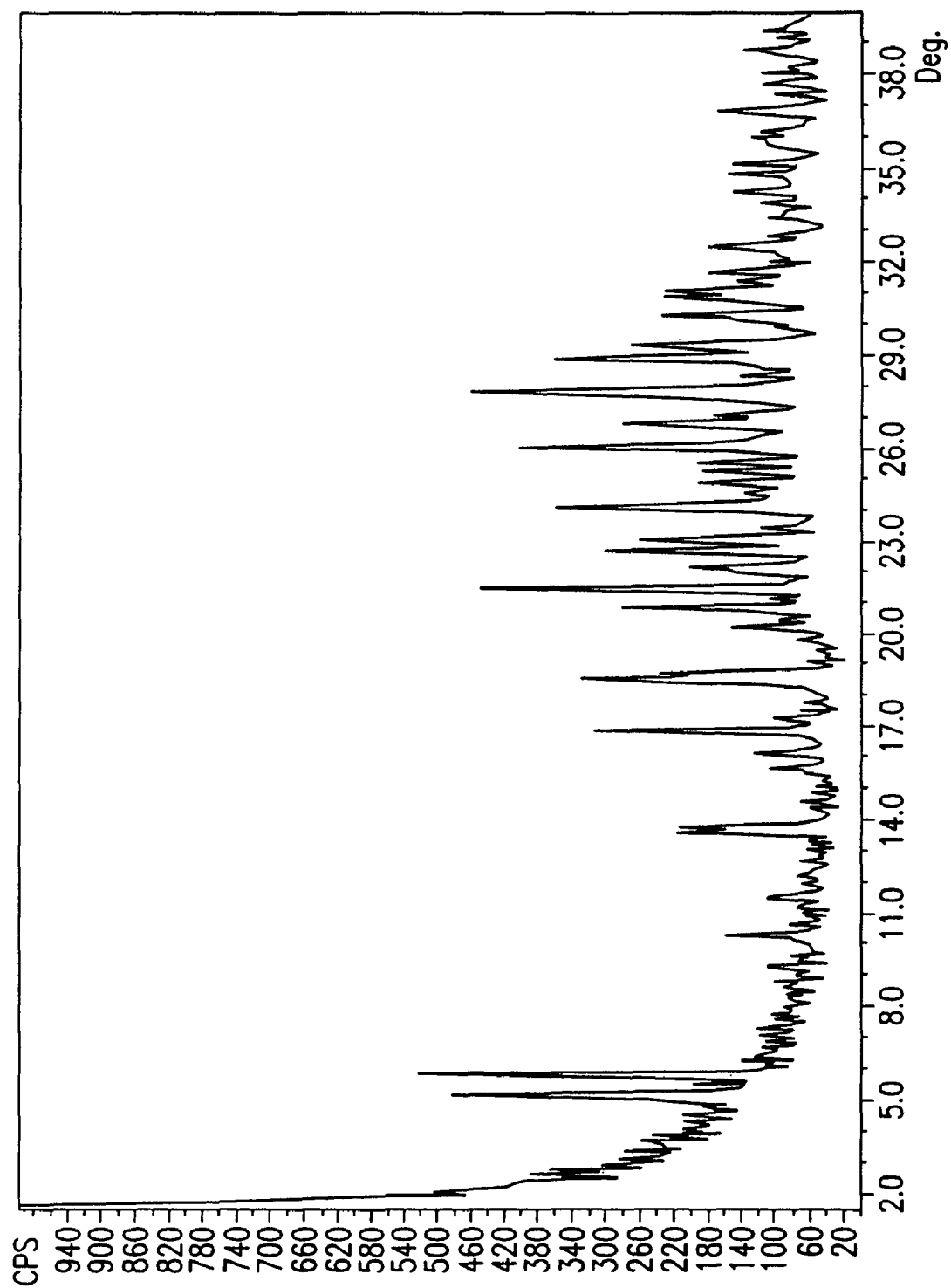

FIG. 11 provides a representative XRPD pattern of Form A of the hydrobromide salt of Compound I.

Figure 12:
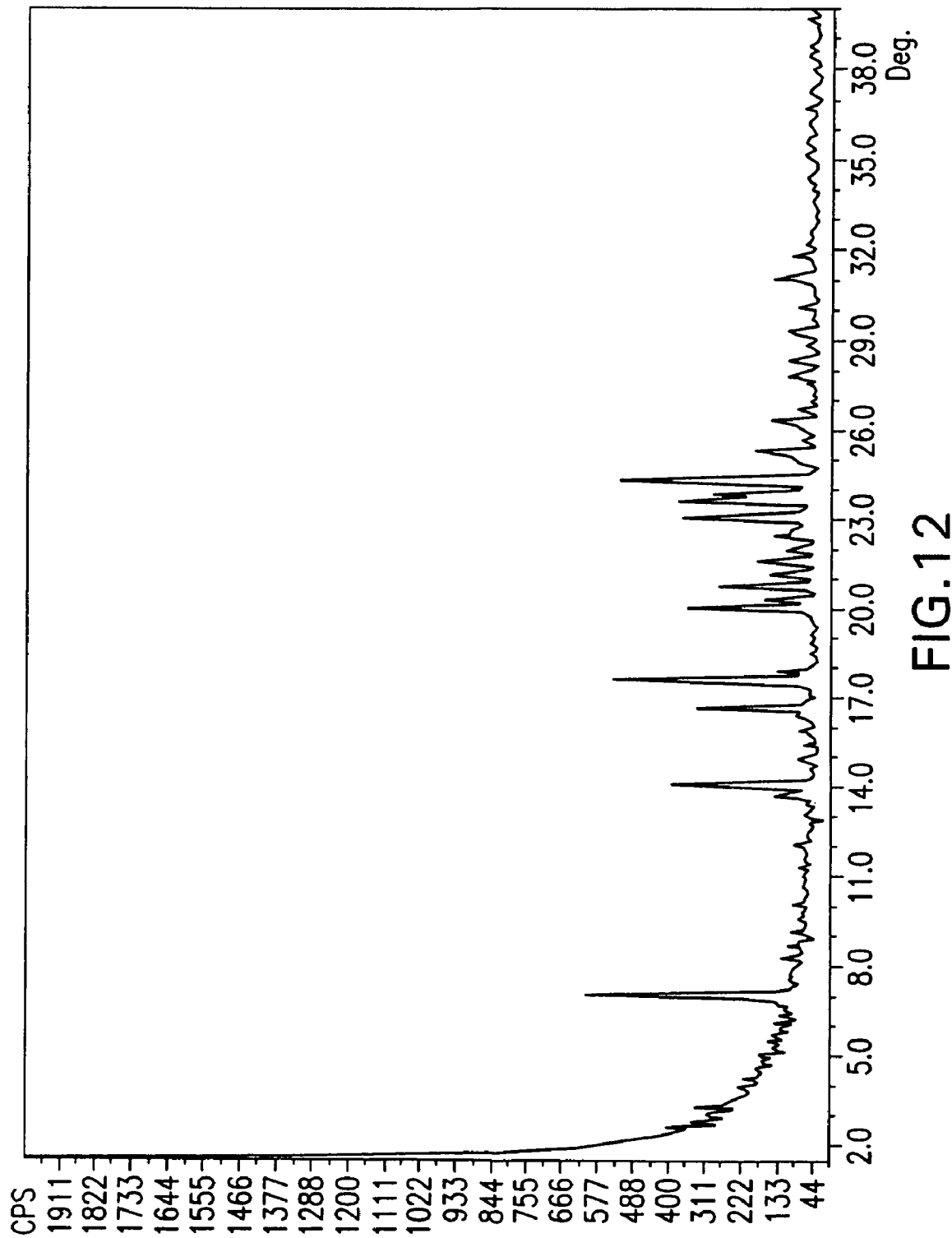

FIG. 12 provides a representative XRPD pattern of Form A of the sulfate salt of Compound I.

Figure 13:
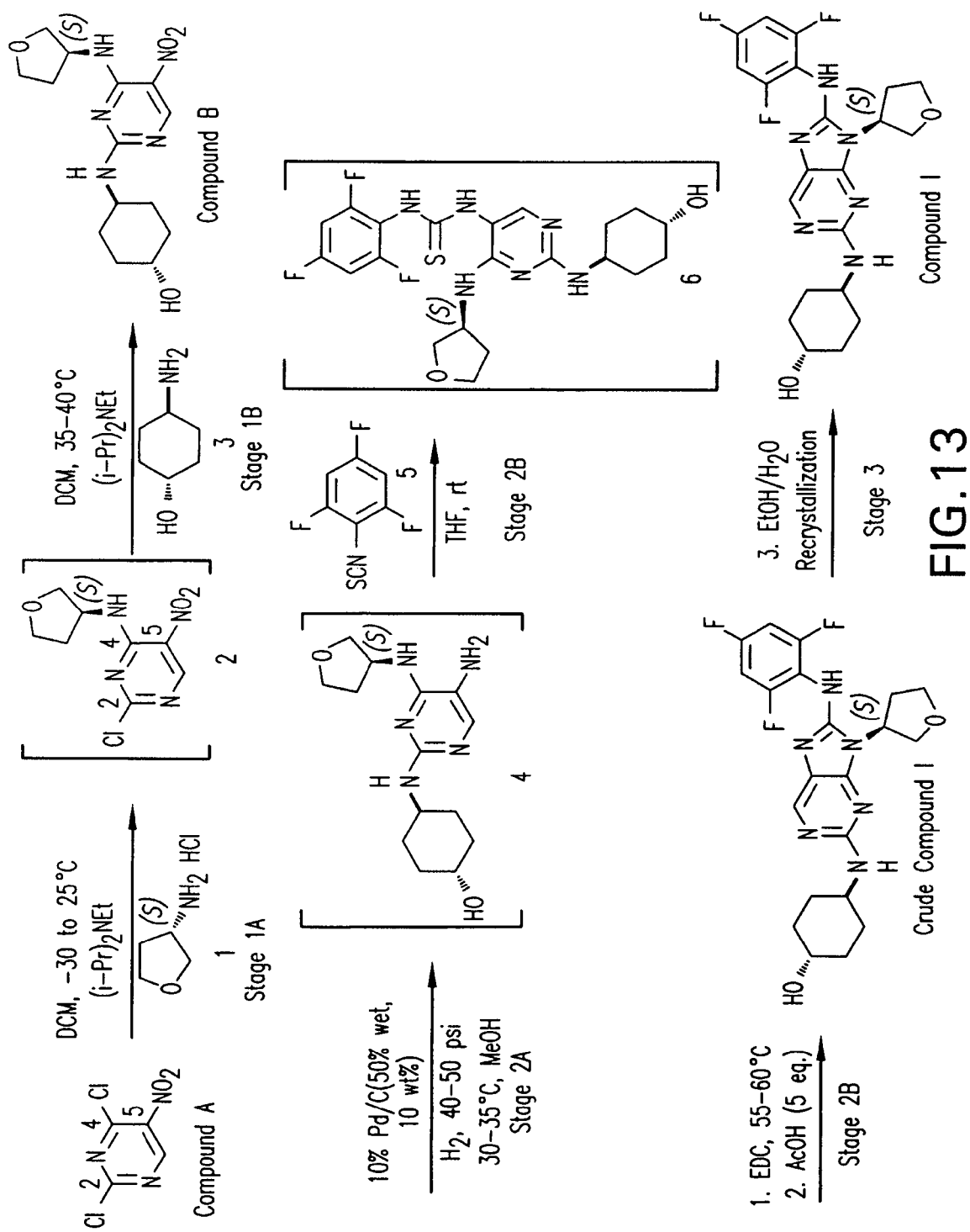

FIG. 13 provides an exemplary reaction scheme for the synthesis of Compound I.

Figure 14:
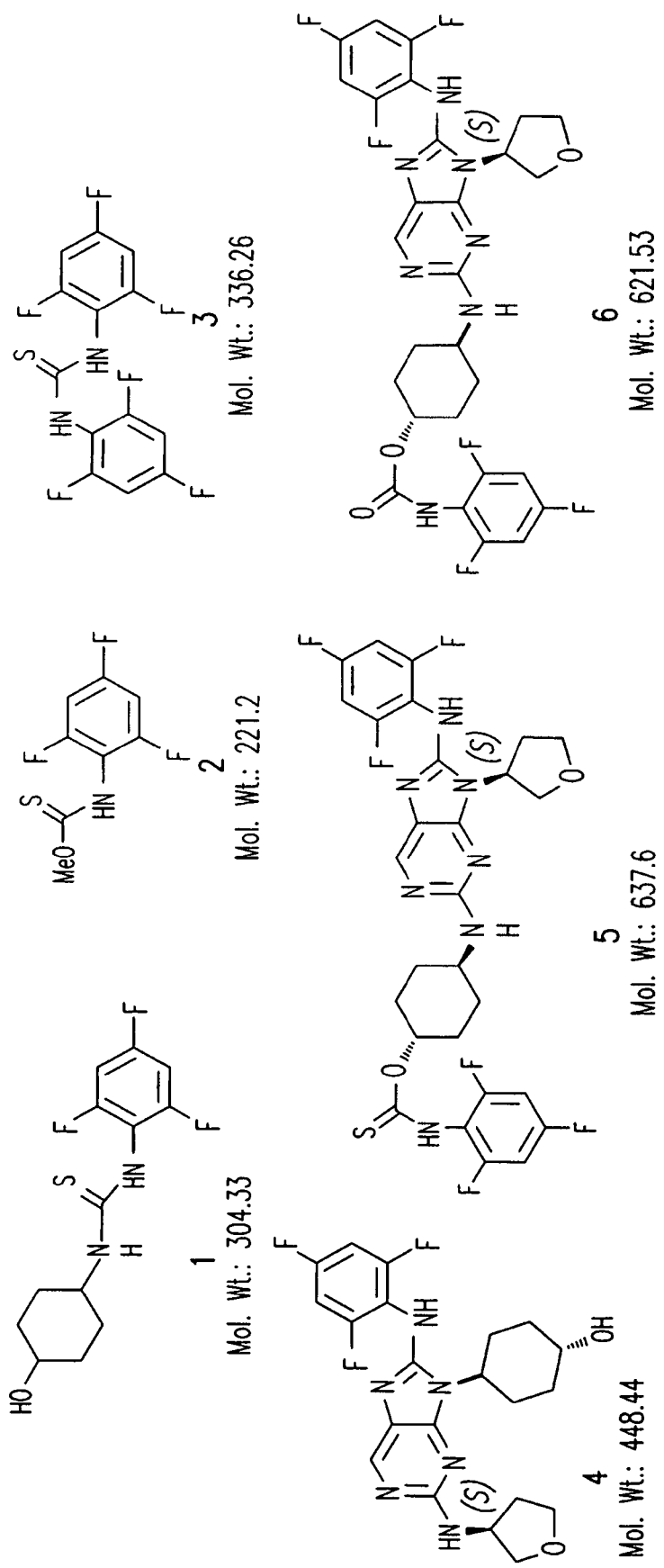

FIG. 14 provides the chemical structures of compounds which, in certain embodiments, may be present in compositions comprising Compound I.

Figure 15:
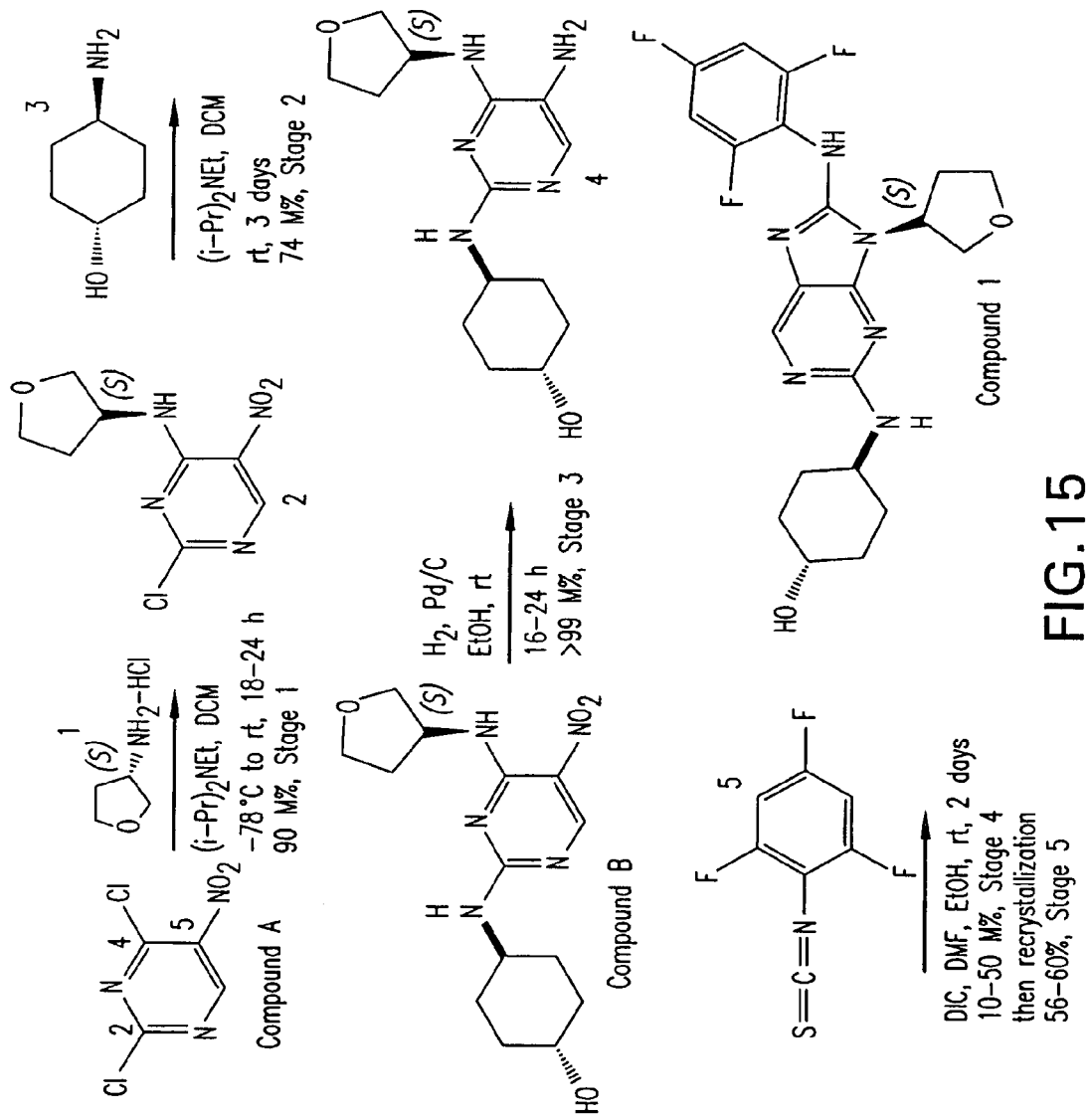

FIG. 15 provides an exemplary reaction scheme for the synthesis of Compound I.

Figure 16:
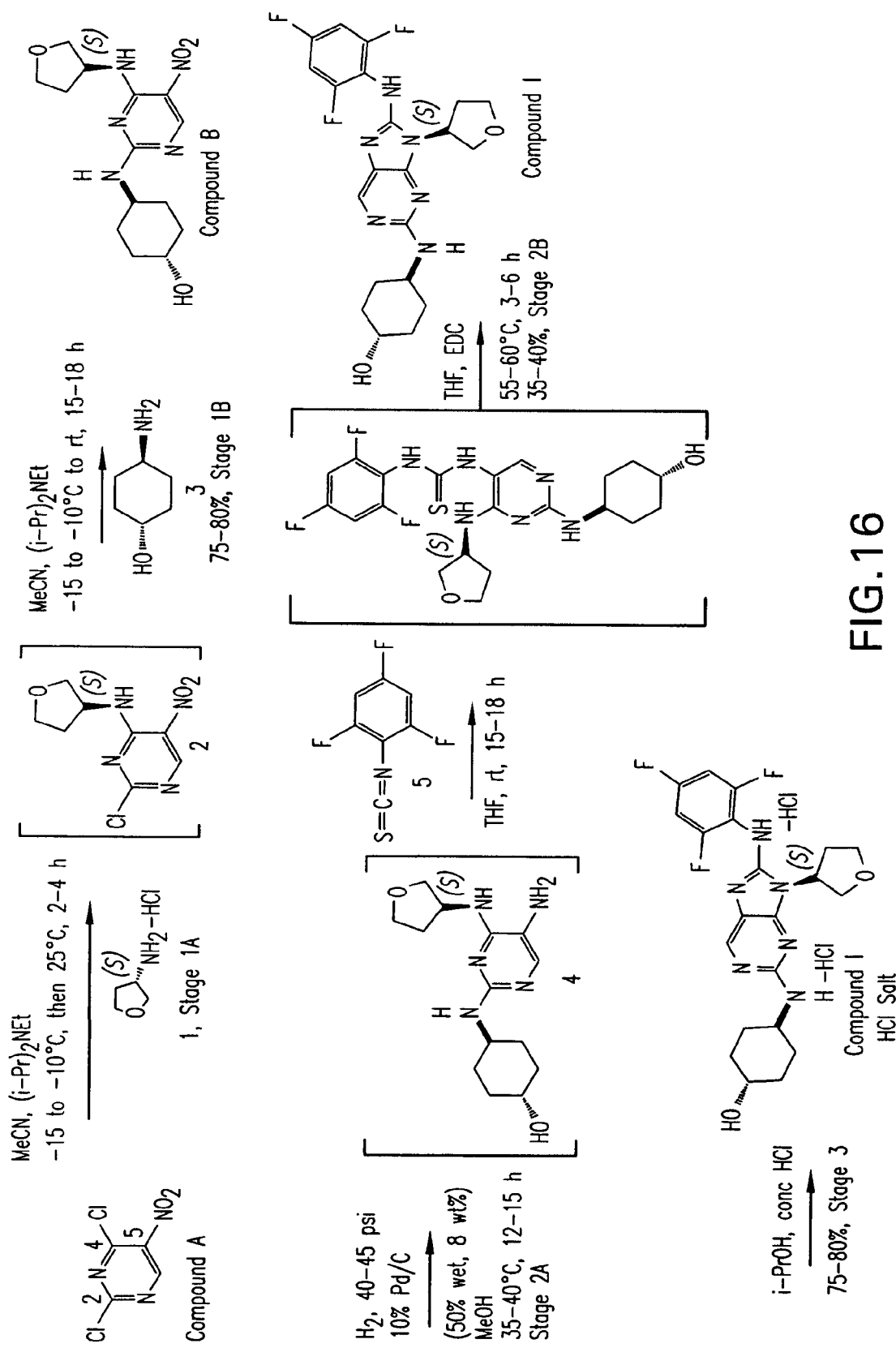

FIG. 16 provides an exemplary reaction scheme for the synthesis of Compound I.

5. DETAILED DESCRIPTION OF THE INVENTION

5.1 Definitions

As used herein, the term "Compound I" means the compound that is chemically named 4-[9-(tetrahydro-furan-3-yl)-8-(2,4,6-trifluoro-phenylamino)-9H-purin-2-ylamino]-cyclohexan-1-ol, and includes its free base form and its ionized forms, which have undergone salt formation such that the molecule is protonated at one or more basic centers. The term "Compound I" also includes the solid forms of 4-[9-(tetrahydro-furan-3-yl)-8-(2,4,6-trifluoro-phenylamino)-9H-purin-2-ylamino]-cyclohexan-1-ol described herein.

Particular salts described below include "hydrochloride salts" or "HCl salts" of Compound I. A hydrochloride salt or HCl salt of Compound I is an acid addition salt which may be formed by reacting Compound I with hydrochloric acid.

A "bis-hydrochloride salt" or "bis-HCl salt" of Compound I is a salt which contains about two molar equivalents of hydrochloric acid per mole of Compound I.

Particular salts described below include "hydrobromide salts" or "HBr salts" of Compound I. A hydrobromide salt or HBr salt of Compound I is an acid addition salt which may be formed by reacting Compound I with hydrobromic acid.

Particular salts described below include "sulfate salts" of Compound I. A sulfate salt of Compound I is an acid addition salt which may be formed by reacting Compound I with sulfuric acid.

As used herein, the term "pharmaceutically acceptable salts" refers to salts prepared from pharmaceutically acceptable acids, including inorganic acids and organic acids. Suitable acids include, but are not limited to, acetic, benzenesulfonic, benzoic, camphorsulfonic, carbonic, citric, dihydrogenphosphoric, ethanesulfonic, fumaric, galactunoric, gluconic, glucuronic, glutamic, hydrobromic, hydrochloric, hydriodic, isobutyric, isethionic, lactic, maleic, malic, malonic, mandelic, methanesulfonic, monohydrogencarbonic, monohydrogenphosphoric, monohydrogensulfuric, mucic, nitric, pamoic, pantothenic, phosphoric, phthalic, propionic, suberic, succinic, sulfuric, tartaric, toluenesulfonic, including p-toluenesulfonic m-toluenesulfonic and o-toluenesulfonic acids, and the like (see, e.g., S. M. Berge et al., *J. Pharm. Sci.*, 66:1-19 (1977); and *Handbook of Pharmaceutical Salts Properties, Selection and Use*, P. H. Stahl and C. G. Wermuth, Eds., (2002), Wiley, Weinheim). Also included are salts of other compounds that possess acidic character, including amino acids, such as aspartic acid and the like, and other compounds, such as aspirin, ibuprofen, saccharin, and the like. Acid addition salts can be obtained by contacting the neutral form of such compounds with a sufficient amount of the desired acid, either neat or in a suitable solvent. As solids, salts can exist in crystalline or amorphous modifications.

The terms "solid form," "solid forms" and related terms, when used herein to refer to Compound I, refer to a physical form comprising Compound I which is not predominantly in a liquid or a gaseous state. Crystal forms and amorphous forms are examples of solid forms.

The term "crystalline" and related terms used herein, when used to describe a substance, component, product, or form, means that the substance, component or product is substantially crystalline as determined by X-ray diffraction. See, e.g., *Remington's Pharmaceutical Sciences*, 18$^{th}$ ed., Mack Publishing, Easton Pa., 173 (1990); *The United States Pharmacopeia*, 23$^{rd}$ ed., 1843-1844 (1995).

The term "crystal form," "crystalline form" and related terms herein refer to a crystalline solid form comprising a chemical compound, and may refer to a particular single-component or multiple-component crystal form, including, but not limited to, a polymorph, a solvate, a hydrate, a cocrystal or other molecular complex, a salt, a solvate of a salt, a hydrate of a salt, a cocrystal or other molecular complex of a salt, or a polymorph thereof.

The terms "polymorphs," "polymorphic forms" and related terms herein refer to two or more crystal forms that comprise the same molecule, molecules or ions. Different polymorphs may have different physical properties such as, for example, melting temperatures, heats of fusion, solubilities, dissolution rates and/or vibrational spectra as a result of the arrangement or conformation of the molecules or ions in the crystal lattice. The differences in physical properties exhibited by polymorphs affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing; for example, one polymorph might be more likely to form solvates or might be difficult to filter and wash free of impurities (e.g., particle shape and size distribution might be different between polymorphs).

The term "solvate" and "solvated," as used herein, refer to a crystal form of a substance which contains solvent. The term "hydrate" and "hydrated" refer to a solvate wherein the solvent is water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which can only be made by removing the solvent from a solvate.

The term "amorphous," "amorphous form," and related terms used herein mean that the substance, component or product in question is not substantially crystalline as determined by X-ray diffraction. In certain embodiments, a sample comprising an amorphous form of a substance may be substantially free of other amorphous forms and/or crystal forms.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, more specifically within 10%, more specifically within 5%, of the specified dose, amount, or weight percent.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies and dissolution studies.

As used herein, and unless otherwise specified, the terms "about" and "approximately," when used in connection with a numeric value or range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. Specifically, the terms "about" and "approximately," when used in this context, indicate that the numeric value or range of values may vary, in particular embodiments, within 20%, 10%, 9%, 8%, 7%, 6%, 5%, 4%, 3%, 2%, 1.5%, 1%, 0.5%, or 0.25% of the recited value or range of values.

As used herein, a solid form (e.g., a crystal form or amorphous form) that is "substantially pure" may comprise, in particular embodiments, less than about 20%, 15%, 10%, 5%, 3%, 2%, 1%, 0.75%, 0.5%, 0.25% or 0.1% by weight of one or more other crystal forms, amorphous forms and/or chemical compounds. In certain embodiments, a solid form that is substantially pure is substantially free of one or more other particular crystal forms, amorphous forms and/or chemical compounds.

As used herein and unless otherwise indicated, a composition that is "substantially free" of a solid form and/or chemical substance contains less than about 20%, 15%, 10%, 5%, 3%, 2%, 1%, 0.75%, 0.5%, 0.25% or 0.1% by weight of the solid form and/or chemical compound.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder.

As used herein, and unless otherwise specified, the terms "prevent," "preventing" and "prevention" refer to the prevention of the onset, recurrence or spread of a disease or disorder, or of one or more symptoms thereof.

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic or therapeutic agent do not result in a cure of the disease or disorder.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant the diluent, excipient or carrier must be compatible with the other ingredients of the formulation and not deleterious to the recipient thereof.

The term "therapeutically and prophylactically effective amount" refers to the amount of the subject solid form that will elicit the biological or medical response of a tissue, system, animal or human that is being sought by the researcher, veterinarian, medical doctor or other clinician or that is sufficient to prevent development of or alleviate to some extent one or more of the symptoms of the disease being treated.

The terms "subject" and "patient," unless otherwise specified, are defined herein to include animals such as mammals, including, but not limited to, primates (e.g., humans), cows, sheep, goats, horses, dogs, cats, rabbits, rats, mice and the like. In specific embodiments, the subject or patient is a human.

In addition to solid forms comprising Compound I, embodiments herein provide solid forms of prodrugs of Compound I. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

In certain embodiments, Compound I may contain unnatural proportions of atomic isotopes at one or more of the atoms. For example, the compound may be radiolabeled with radioactive isotopes, such as for example tritium ($^3$H), iodine-125 ($^{125}$I) sulfur-35 ($^{35}$S), or carbon-14 ($^{14}$C). Radiolabeled compounds are useful as therapeutic agents, e.g., cancer therapeutic agents, research reagents, e.g., binding assay reagents, and diagnostic agents, e.g., in vivo imaging agents. All isotopic variations of the Compound I, whether radioactive or not, are intended to be encompassed within the scope of the embodiments provided herein.

5.2 Solid Forms Comprising Compound I

Certain embodiments herein provide single-component and multiple-component solid forms comprising 4-[9-(tetrahydro-furan-3-yl)-8-(2,4,6-trifluoro-phenylamino)-9H-purin-2-ylamino]-cyclohexan-1-ol ("Compound I"), which has the chemical structure shown below:

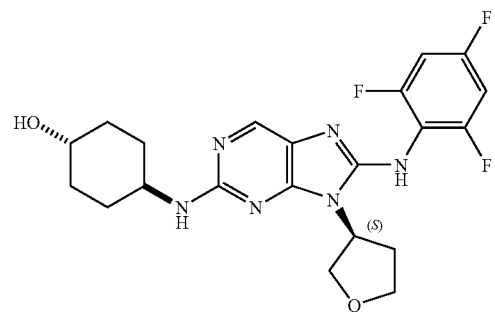

Compound I can be synthesized or obtained according to any method apparent to those of skill in the art based upon the teachings herein, including the methods described in detail in the examples below. Compound I can also be prepared according to the methods described in U.S. patent application Ser. No. 11/332,617, filed Jan. 12, 2006, and International Pub. No. WO 2006/076595, the entireties of each of which is incorporated by reference herein.

In certain embodiments, Compound I is prepared by a process comprising the steps of: (1) substitution of a nitropyrimidine with an amine-containing compound (e.g., an amine-containing heterocycle, such as an amine-substituted tetrahydrofuran) or salt thereof; (2) further substitution with an additional amine-containing compound (e.g., amine-containing carbocycle, such as an amine-substituted cyclohexanol) or salt thereof; (3) reduction of the nitro group to the corresponding amine (e.g., to substituted aniline); (4) coupling with an isothiocyanate substituted aryl or heteroaryl compound (e.g., 2,4,6-trifluorophenyl isothiocyanate); and (5) ring closure resulting in substituted purine formation. In certain embodiments, two or more of the steps of the process may be combined and/or conducted in sequence without isolation of intermediate compound(s). In certain embodiments, the steps of the process are performed in the order in which they are listed. In certain embodiments, the steps of the process are performed in an order other than that in which they are listed.

In a particular embodiment, step (1) is carried out in the presence of N,N-diisopropylethylamine (DIPEA). In another particular embodiment, step (2) is carried out in the presence of DIPEA. In another particular embodiment, step (3) is carried out in the presence of Pd catalyst. In another particular embodiment, step (4) is carried out in THF. In another particular embodiment, step (5) is carried out in the presence of N-(3-Dimethylaminopropyl)-N'-ethylcarbodiimide hydrochloride (EDC).

Solid forms comprising Compound I provided herein include single-component and multiple-component forms, including crystal forms and amorphous forms, and including, but not limited to, polymorphs, salts, solvates, hydrates, co-crystals and clathrates. Solid forms provided herein can be prepared by the methods described herein, including the methods described in detail in the examples below, or by techniques known in the art, including heating, melt cooling, rapid melt cooling, freeze drying, lyophilization, quench cooling the melt, rapid solvent evaporation, slow solvent evaporation, solvent recrystallization, slurry recrystallization, crystallization from the melt, desolvation, sublimation, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid cooling, slow cooling, vapor diffusion, sublimation, grinding, cryo-grinding, solvent-drop grinding, microwave-induced precipitation, ultrasonication-induced precipitation, laser-induced precipitation and precipitation from a supercritical fluid.

Particular embodiments herein provide compositions comprising one or more of the solid forms. Certain embodiments herein provide to compositions of one or more solid forms in combination with other active ingredients. Certain embodiments herein provide methods of using these compositions in the treatment, prevention or management of conditions and disorders including, but not limited to, cancer, a cardiovascular disease, a renal disease, an autoimmune condition, an inflammatory condition, macular degeneration, ischemia-reperfusion injury, pain and related syndromes, disease-related wasting, an asbestos-related condition, pulmonary hypertension, central nervous system (CNS) injury/damage or a condition treatable or preventable by inhibition of a kinase pathway.

Particular embodiments herein provide a composition comprising a crystal form and/or an amorphous form of Compound I further comprising one or more of the compounds provided in FIG. 14. In specific embodiments, a composition comprising a crystal form and/or an amorphous form of Compound I further comprises a compound provided in FIG. 14 in an amount of less than about 0.01%, 0.05%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5%, 6%, 7%, 8%, 9% or 10% of the total amount of Compound I in the composition on a weight basis.

While not intending to be bound by any particular theory, certain solid forms provided herein are characterized by physical properties, e.g., stability, solubility and dissolution rate, appropriate for clinical and therapeutic dosage forms. Moreover, while not wishing to be bound by any particular theory, certain salts and crystal forms provided herein are characterized by physical properties, e.g., crystal morphology, compressibility and hardness, suitable for manufacture of a solid dosage form. Such properties can be determined using techniques such as X-ray diffraction, microscopy, IR spectroscopy and thermal analysis, as described herein and known in the art.

5.2.1 Single-Component Solid Forms of Compound I

Certain embodiments herein provide single-component solid forms of the free base of 4-[9-(tetrahydro-furan-3-yl)-8-(2,4,6-trifluoro-phenylamino)-9H-purin-2-ylamino]-cyclohexan-1-ol ("Compound I") having utility for the treatment, prevention or management of conditions and disorders including, but not limited to, cancer, a cardiovascular disease, a renal disease, an autoimmune condition, an inflammatory condition, macular degeneration, ischemia-reperfusion injury, pain and related syndromes, disease-related wasting, an asbestos-related condition, pulmonary hypertension, central nervous system (CNS) injury/damage or a condition treatable or preventable by inhibition of a kinase pathway.

Certain embodiments herein provide single-component amorphous solid forms of the free base of Compound I. Certain embodiments herein provide single-component crystal forms, or polymorphs, of the free base of Compound I.

The single-component solid forms of Compound I can be prepared by any method apparent to those skilled in the art based upon the teachings herein. The single-component solid forms of Compound I can also be prepared according to the techniques described herein, including the methods described in detail in the examples below.

As described below, certain single-component solid forms of Compound I display superior properties in comparison to other solid forms of Compound I.

5.2.1.1 Form A of the Free Base of Compound I

Certain embodiments herein provide the Form A crystal form of the free base of Compound I. In certain embodiments, Form A of the free base of Compound I can be obtained by a procedure comprising evaporating a solution of the free base in one or more solvents including, but not limited to, acetone, n-butanol, ethanol, methanol, 2-propanol, tetrahydrofuran (THF), ethanol/water (1/1) and mixtures of two more thereof. In certain embodiments, the evaporation may be performed, e.g., at about 25° C. or about 50° C. In certain embodiments, Form A of the free base of Compound I can be obtained by a procedure comprising slurrying the free base in one or more solvents, including, but not limited to, acetone, acetonitrile, n-butanol, ethanol, ethyl acetate, heptane, methylene chloride, methyl ethyl ketone, methyl t-butyl ether (MTBE), 2-propanol, toluene, water, ethanol/water (1/1) and mixtures of two more thereof. In certain embodiments, the slurry may be performed, e.g., at about 25° C. or about 50° C. In certain embodiments, Form A of the free base of Compound I can be obtained by a procedure comprising solvent/antisolvent precipitation, including, but not limited to, ethanol/water, ethanol/MTBE, ethanol/heptane, THF/MTBE, THF/heptane and THF/toluene solvent systems. In certain embodiments, the precipitation may be performed, e.g., at solvent/antisolvent ratios of about 1/10 and at temperatures of about 50° C. In certain embodiments, Form A of the free base of Compound I can be obtained by a procedure comprising slurrying another solid form comprising the free base of Compound I (e.g., a hydrate of Compound I) in a solvent, such as, e.g., acetonitrile, heptane, ethyl acetate, MTBE, toluene and mixtures of two or more thereof. In certain embodiments, Form A of the free base of Compound I can be obtained from various solvents, including, but not limited to, ethanol, water, and an ethanol/water mixture.

A representative XRPD pattern of Form A of the free base of Compound I is provided in FIG. 1. In certain embodiments, Form A of the free base of Compound I is characterized by XRPD peaks located at one or more of the following approximate positions: 10.0, 12.4, 12.8, 15.2, 16.0, 16.3, 17.7, 18.5, 18.9, 19.4, 20.0, 20.6, 20.9, 21.6, 22.7, 23.2, 26.1, 26.6, 26.8, 25.7, 26.0, 26.4, 26.6, 27.2, 27.9, 30.2, 30.8, 31.0, 31.5 degrees 2θ. In particular embodiments, Form A of the free base of Compound I is characterized by XRPD peaks located at one, two, three, four, five or six of the following approximate positions: 12.4, 16.0, 17.7, 18.5, 23.2, 24.1 degrees 2θ. In certain embodiments, Form A of the free base of Compound I has an XRPD pattern comprising peaks at approximately 12.4, 16.0 and 18.5 °2θ. In certain embodiments, Form A of the free base of Compound I has an XRPD pattern further comprising peaks at approximately 17.7, 23.2 and 24.1 °2θ.

Representative thermal characteristics of Form A of the free base of Compound I are shown in FIG. 2 and FIG. 3. A representative DSC thermogram, presented in FIG. 2, exhibits an endothermic event with an onset temperature at about 225° C. In particular embodiments, the thermal event at about 225° C. is a melting event. In particular embodiments, Form A melts at about 225.0° C. A representative TGA thermogram, presented in FIG. 3, exhibits a small mass loss, on the order of less than about 1% of the total mass of the sample, upon heating from ambient temperature to about 200° C. The thermal data indicate that Form A of the free base of Compound I does not contain substantial amounts of either water or solvent in the crystal lattice. In certain embodiments, Form A is unsolvated. In certain embodiments, Form A is anhydrous.

Form A of the free base of Compound I exhibits desirable characteristics for the synthesis, processing and manufacture of drug product containing Compound I. For example, in certain embodiments, Form A of the free base of Compound I has an advantageous stability profile, which is an important characteristic for processing and manufacturing. In certain embodiments, Form A of the free base of Compound I is stable during drying at temperatures up to about 40-45° C. In certain embodiments, the crystallization and/or recrystallization of Form A of the free base of Compound I provides an effective means of purification by removing or reducing the levels of chemical impurities (such as, e.g., one or more of the chemical compounds provided in FIG. 14) in the resulting material. In certain embodiments, Form A of the free base of Compound I is substantially pure. In certain embodiments, Form A of the free base of Compound I is non-hygroscopic, e.g., exhibits a mass gain of less than about 2% of when subjected to an increase in humidity from about 0% to about 80% relative humidity (RH). For example, in certain embodiments, when subjected to moisture sorption analysis, Form A exhibits a mass gain of about 0.5% when increased from about 0% to about 80% RH, and exhibits a mass gain of about 1.4% when increased from about 0% to about 95% RH. In certain embodiments, following moisture sorption analysis, the XRPD pattern of the Form A material is substantially unchanged. In certain embodiments, Form A of the free base of Compound I is stable upon compression. For example, in certain embodiments, when subjected to compression testing involving about 2000-psi pressure for about 1 min, the XRPD pattern of Form A is substantially unchanged.

Certain embodiments herein provide the Form A crystal form of the free base of Compound I which is substantially pure. In particular embodiments, a sample of substantially pure Form A is substantially free of other solid forms, including other solid forms comprising Compound I, such as, e.g., other solid forms comprising Compound I described herein. In particular embodiments, a sample of substantially pure Form A is substantially free of other chemical compounds, including, e.g., solvent, water, and/or the compounds depicted in FIG. 14.

5.2.1.2 Form B of the Free Base of Compound I

Certain embodiments herein provide the Form B crystal form of the free base of Compound I. In certain embodiments, Form B has an onset melting temperature at approximately 213° C., as measured, e.g., by DSC. In certain embodiments, the Form B crystal form of the free base of Compound I may be prepared, e.g., by heating a hydrate form of the free base of Compound I above about 185° C. Characterization data for Form B of the free base of Compound I is provided in FIG. 5, in which a hydrate of the free base of Compound I is converted into Form B of the free base of Compound I by dehydration upon heating.

5.2.2 Multiple-Component Solid Forms of Compound I

Certain embodiments herein provide multiple-component solid forms comprising Compound I having utility for the treatment, prevention or management of conditions and disorders including, but not limited to, cancer, a cardiovascular disease, a renal disease, an autoimmune condition, an inflammatory condition, macular degeneration, ischemia-reperfusion injury, pain and related syndromes, disease-related wasting, an asbestos-related condition, pulmonary hypertension, central nervous system (CNS) injury/damage or a condition treatable or preventable by inhibition of a kinase pathway.

Certain embodiments herein provide multiple-component amorphous forms comprising Compound I. Certain embodiments herein provide multiple-component crystal forms comprising Compound I. The multiple-component solid forms comprising Compound I may be neutral or ionic complexes, or may comprise both neutral and ionic components together in the solid form. Multiple-component solid forms provided herein include solid forms which may be described by the terms salt, co-crystal, hydrate, solvate, clathrate and/or polymorph, and include solid forms which may be accurately described by one or more of these terms.

The multiple-component solid forms comprising Compound I can be prepared by any method apparent to those skilled in the art based upon the teachings herein. The multiple-component solid forms of Compound I can also be prepared according to the techniques described herein, including the methods described in detail in the examples below.

As described below, certain multiple-component solid forms of Compound I display superior properties in comparison to other solid forms of Compound I.

5.2.2.1 Hydrate of the Free Base of Compound I

Certain embodiments herein provide a hydrate crystal form of the free base of Compound I. In certain embodiments, this hydrate of the free base of Compound I can be obtained by precipitating Compound I from various solvents, including, but not limited to, ethanol, water or a mixture thereof. In certain embodiments, this hydrate of the free base of Compound I can be obtained by precipitation following a cooling procedure. In certain embodiments, the ratio of water in the resulting product can be confirmed using elemental analysis, Karl Fischer analysis, thermal gravimetric (TG) analysis, TG coupled with infrared spectroscopy analysis (TG/IR), TG coupled with mass spectrometry analysis (TG/MS) and/or crystal structure determination. In certain embodiments, the hydrate of the free base of Compound I contains about 0.5, 1.0, 1.5, 2.0, 2.5, 3.0, 3.5, 4.0, 4.5 or 5.0 molar equivalents of water per mole of Compound I in the crystal lattice. In certain embodiments, the hydrate contains about 9% water on a weight basis. In certain embodiments, the hydrate material can be dehydrated, e.g., by heating above at temperature of about 100° C.

A representative XRPD pattern of this hydrate of the free base of Compound I is provided in FIG. 4. In certain embodiments, the hydrate crystal form of the free base of Compound I is characterized by XRPD peaks located at one or more of the following approximate positions: 6.5, 9.2, 10.3, 11.2, 13.0, 13.4, 15.9, 18.4, 19.5, 20.1, 20.5, 21.1, 21.5, 21.8, 23.0, 23.8, 24.7, 25.6, 26.0, 26.8 degrees 2θ. In particular embodiments, the hydrate crystal form of the free base of Compound I is characterized by XRPD peaks located at one, two, three, four, five, six or seven of the following approximate positions: 6.5, 13.0, 13.4, 19.5, 20.1, 23.0, 23.8 degrees 2θ. In certain embodiments, the hydrate crystal form of the free base of Compound I has an XRPD pattern comprising peaks at approximately 6.5, 13.0 and 23.0 °2θ. In certain embodiments, the hydrate crystal form of the free base of Compound I has an XRPD pattern further comprising peaks at approximately 13.4, 20.1 and 23.8 °2θ.

Representative thermal characteristics of this hydrate of the free base of Compound I are shown in FIG. 5 and FIG. 6. A representative DSC thermogram, presented in FIG. 5, exhibits initial endothermic events with peak temperatures at about 79° C. and about 95° C., followed by an exothermic event with a peak temperature at about 181° C., followed by two endothermic events with onset temperatures at about 215° C. and about 227° C. A representative TGA thermogram, presented in FIG. 6, exhibits a mass loss of about 10% of the total mass of the sample upon heating from ambient temperature to about 200° C. TG/IR analysis indicated that the mass loss comprised a loss of water.

This hydrate crystal form of the free base of Compound I exhibits desirable characteristics for the synthesis, processing and manufacture of drug product containing Compound I. For example, the crystallization or recrystallization of this hydrate of the free base of Compound I provides an effective means of purification. In certain embodiments, the hydrate of the free base of Compound I is substantially pure.

5.2.2.2 Form A of the HCl Salt of Compound I

Certain embodiments herein provide the Form A crystal form of the HCl salt of Compound I. In certain embodiments, Form A of the HCl salt of Compound I can be obtained by reacting Compound I with HCl in various solvents, including, but not limited to, ethanol, isopropanol, water or mixtures thereof. The HCl may be charged to the reaction as a solution, e.g., a concentrated aqueous solution, or as a gas. In certain embodiments, the stoichiometry of the resulting product can be confirmed, e.g., using elemental analysis for chlorine. In certain embodiments, the HCl salt of Compound I contains approximately two molar equivalents of chloride ion per mole of Compound I. In certain embodiments, the Form A of the HCl salt of Compound I is a bis-HCl salt of Compound I. In certain embodiments, Form A of the HCl salt of Compound I can be prepared, e.g., by precipitation following evaporation (e.g., at about 25° C. or about 50° C.) from solutions of the HCl salt in solvents including, but not limited to, n-butanol, ethanol, methanol, 2-propanol, water, ethanol/water (1/1), and mixtures of two or more thereof. In certain embodiments, Form A of the HCl salt of Compound I can be prepared, e.g., by slurrying the HCl salt (e.g., at about 25° C. or about 50° C.) in solvents including, but not limited to, acetone, acetonitrile, n-butanol, ethyl acetate, heptane, methylene chloride, methyl ethyl ketone, MTBE, 2-propanol, toluene and THF, and mixtures of two or more thereof.

A representative XRPD pattern of Form A of the HCl salt of Compound I is provided in FIG. 7. In certain embodiments, Form A of the HCl salt of Compound I is characterized by XRPD peaks located at one or more of the following approximate positions: 5.2, 6.1, 14.2, 17.3, 18.7, 21.1, 21.9, 22.4, 23.5, 24.8, 27.7, 29.3, 31.2 degrees 2θ. In particular embodiments, Form A of the HCl salt of Compound I is characterized by XRPD peaks located at one, two, three, four or five of the following approximate positions: 17.3, 18.7, 21.1, 22.4, 23.5, 24.8 degrees 2θ. In certain embodiments, Form A of the HCl salt of Compound I has an XRPD pattern comprising peaks at approximately 17.3, 18.7 and 22.4 °2θ. In certain embodiments, Form A of the HCl salt of Compound I has an XRPD pattern comprising peaks approximately 21.1, 23.5 and 24.8 °2θ. In certain embodiments, Form A of the HCl salt of Compound I has an XRPD pattern comprising a peak located at least one of the following two positions: 5.2, 6.1 degrees degrees 2θ.

Representative thermal characteristics of Form A of the HCl salt of Compound I are shown in FIG. 9 and FIG. 10. A representative DSC thermogram, presented in FIG. 9 exhibits an initial broad endothermic event followed by another endothermic event with an onset temperature at about 170° C. A representative TGA thermogram, presented in FIG. 10, exhibits a mass loss on the order of between about 1-2% of the total mass of the sample upon heating from ambient temperature to about 125° C.

Form A of the HCl salt of Compound I exhibits desirable characteristics for the synthesis, processing and manufacture of drug product containing Compound I. For example, in certain embodiments, the crystallization or recrystallization of Form A of the HCl salt of Compound I provides an effective means of purification by removing or reducing the levels of chemical impurities in the resulting drug substance. In certain embodiments, Form A of the HCl salt of Compound I is substantially pure. In certain embodiments, Form A of the HCl salt of Compound I is stable upon slurry in particular solvents at particular temperatures. For example, in certain embodiments, Form A of the HCl salt is stable in, e.g., acetone, acetonitrile, ethyl acetate, heptane, MTBE, toluene, THF and mixtures of two or more thereof at about 40° C. for about four weeks. In certain embodiments, Form A of the HCl salt is stable upon storage at particular stress conditions. For example, in certain embodiments, Form A of the HCl salt of Compound I is stable upon storage at about 40° C. and about 75% RH for about four weeks.

5.2.2.3 Form A of the HBr Salt of Compound I

Certain embodiments herein provide the Form A crystal form of the HBr salt of Compound I. In certain embodiments, Form A of the HBr salt of Compound I can be obtained by reacting Compound I with HBr in various solvents, including, but not limited to, ethanol, isopropanol, water or mixtures thereof. The HBr may be charged to the reaction as a solution, e.g., a concentrated aqueous solution, or as a gas. A representative XRPD pattern of Form A of the HBr salt of Compound I is provided in FIG. 11. In certain embodiments, Form A of the HBr salt of Compound I is characterized by XRPD peaks located at one or more of the following approximate positions: 5.1, 5.8, 16.9, 18.5, 18.7, 20.9, 21.5, 22.7, 23.1, 24.1, 26.0, 26.8, 27.8, 28.9, 29.3 degrees 2θ. In particular embodiments, Form A of the HBr salt of Compound I is characterized by XRPD peaks located at one, two, three, four, or five of the following approximate positions: 5.1, 5.8, 18.5, 21.5, 27.8 degrees 2θ.

Form A of the HBr salt of Compound I exhibits desirable characteristics for the synthesis, processing and manufacture of drug product containing Compound I. For example, the crystallization or recrystallization of Form A of the HBr salt of Compound I provides an effective means of purification by removing or reducing the levels of chemical impurities in the resulting drug substance. In certain embodiments, Form A of the HBr salt of Compound I is substantially pure.

5.2.2.4 Form A of the Sulfate Salt of Compound I

Certain embodiments herein provide the Form A crystal form of the sulfate salt of Compound I. In certain embodiments, Form A of the sulfate salt of Compound I can be obtained by reacting Compound I with sulfuric acid in various solvents, including, but not limited to, ethanol, isopropanol, water or mixtures thereof.

A representative XRPD pattern of Form A of the sulfate salt of Compound I is provided in FIG. 12. In certain embodiments, Form A of the sulfate salt of Compound I is characterized by XRPD peaks located at one or more of the following approximate positions: 7.0, 14.1, 16.7, 17.6, 17.9, 19.9, 20.3, 20.8, 21.2, 21.7, 23.1, 23.7, 23.9, 24.3, 25.3 degrees 2θ. In particular embodiments, Form A of the sulfate salt of Compound I is characterized by XRPD peaks located at one, two, three, four or five of the following approximate positions: 7.0, 14.1, 17.6, 23.7, 24.3 degrees 2θ. In certain embodiments, Form A of the sulfate salt of Compound I is substantially pure.

5.3 Methods of Use

The solid forms comprising Compound I have utility as pharmaceuticals to treat, prevent and/or manage disease in animals or humans. Further, the solid forms comprising Compound I are active against protein kinases including those involved in cancer, inflammatory conditions, immunological conditions, neurodegenerative diseases, cardiovascular diseases, metabolic conditions, insulin resistance, diabetes, fibrotic diseases, and disorders caused, induced or exacerbated by ozone, cold or exercise. Accordingly, provided herein are many uses of the solid forms comprising Compound I, including the treatment or prevention of those diseases set forth below, as well as those described in U.S. patent application Ser. No. 11/332,617, filed Jan. 12, 2006, and International Pub. No. WO 2006/076595, U.S. patent application Ser. No. 11/411,413, filed Apr. 26, 2006, published as U.S. Pat. App. Pub. No. 2007/0060598 on Mar. 15, 2007, and U.S. patent application Ser. No. 11/708,150, filed Feb. 15, 2007, the entireties of each of which is incorporated by reference herein.

Representative immunological conditions that the solid forms comprising Compound I are useful for treating or preventing include, but are not limited to, rheumatoid arthritis, rheumatoid spondylitis, osteoarthritis, multiple sclerosis, lupus, inflammatory bowel disease, ulcerative colitis, Crohn's disease, myasthenia gravis, Grave's disease and diabetes (e.g., Type I diabetes).

Representative inflammatory conditions that the solid forms comprising Compound I are useful for treating or preventing include, but are not limited to, asthma and allergic rhinitis, bronchitis, chronic obstructive pulmonary disease, cystic fibrosis, inflammatory bowel disease, irritable bowel syndrome, Crohn's disease, mucous colitis, ulcerative colitis, (e.g., Type I diabetes and Type II diabetes) and obesity.

Representative metabolic conditions that the solid forms comprising Compound I are useful for treating or preventing include, but are not limited to, obesity and diabetes (e.g., Type II diabetes).

Representative cardiovascular diseases that the solid forms comprising Compound I are useful for treating or preventing include, but are not limited to, stroke, myocardial infarction or iscehmic damage to the heart, lung, gut, kidney, liver, pancreas, spleen or brain.

Representative cardiovascular and renal diseases that stent or stent graft coated with or containing a solid form comprising Compound I is useful for treating or preventing include atherosclerosis and the treatment or prevention of restenosis after vascular intervention such as angioplasty.

Representative neurodegenerative diseases that the solid forms comprising Compound I are useful for treating or preventing include, but are not limited to, Huntington's disease, Alzheimer's disease and HIV-associated encephalitis.

Representative disorders caused, induced or exacerbated by ozone, cold or exercise include, but are not limited to, asthma, bronchitis, rhinitis, chronic obstructive pulmonary disease, lung inflammation or airway hyperresponsiveness.

In another embodiment, provided herein are methods for the treatment or prevention of syndrome X or metabolic syndrome.

In a particular embodiment, provided herein are methods for the treatment or prevention of insulin resistance. In certain embodiments, provided herein are methods for the treatment or prevention of insulin resistance that leads to diabetes (e.g., Type II diabetes).

In another embodiment, provide herein are methods for the treatment or prevention of diabetes. Representative diabetes that the solid forms comprising Compound I are useful for treating or preventing include, but are not limited to, Type II diabetes, Type I diabetes, slow-onset Type I diabetes, diabetes insipidus, diabetes mellitus, gestational diabetes mellitus, maturity-onset diabetes, juvenile diabetes, insulin-dependant diabetes, non-insulin dependant diabetes, malnutrition-related diabetes, ketosis-prone diabetes, pre-diabetes, cystic fibrosis related diabetes or ketosis-resistant diabetes.

In another embodiment, provided herein are methods for the treatment or prevention of fibrotic diseases and disorders. Representative fibrotic diseases that the solid forms comprising Compound I are useful for treating or preventing include, but are not limited to, idiopathic pulmonary fibrosis, myelofibrosis, hepatic fibrosis, renal fibrosis, chronic allograft nephropathy, glomerulonephritis, steatofibrosis or steatohepatitis.

A solid form comprising Compound I containing or coated stent or stent graft can further comprise an effective amount of another active agent useful for treating or preventing a cardiovascular or renal disease, including, but are not limited to, an anticoagulant agent, an antimetabolite agent, an anti-inflammatory agent, an antiplatelet agent, an antithrombin agent, an antimitotic agent, a cytostatic agent or an antiproliferative agent.

The solid forms comprising Compound I are also useful for treating or preventing ischemia/reperfusion injury in general. Accordingly, the solid forms comprising Compound I are useful for treating or preventing acute or chronic organ transplant rejection and for the preservation of tissue and organs.

Representative cancers that the solid forms comprising Compound I are useful for treating or preventing include, but are not limited to, cancers of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

Cancers within the scope of the methods provided herein include those associated with BCR-ABL, and mutants or isoforms thereof, as well as kinases from the src kinase family, kinases from the Rsk kinase family, kinases from the CDK family, kinases from the MAPK kinase family, and tyrosine kinases such as Fes, Lyn, and Syk kinases, and mutants or isoforms thereof.

In a particular embodiment, provided herein are methods for the treatment or prevention of a disease or disorder associated with the modulation, for example inhibition, of a kinase, including, but are not limited to, tyrosine-protein kinase (SYK), tyrosine-protein kinase (ZAP-70), protein tyrosine kinase 2 beta (PYK2), focal adhesion kinase 1

(FAK), B lymphocyte kinase (BLK), hemopoietic cell kinase (HCK), v-yes-1 Yamaguchi sarcoma viral related oncogene homolog (LYN), T cell-specific protein-tyrosine kinase (LCK), proto-oncogene tyrosine-protein kinase (YES), proto-oncogene tyrosine-protein kinase (SRC), proto-oncogene tyrosine-protein kinase (FYN), proto-oncogene tyrosine-protein kinase (FGR), proto-oncogene tyrosine-protein kinase (FER), proto-oncogene tyrosine-protein kinase (FES), C-SRC kinase, protein-tyrosine kinase (CYL), tyrosine protein kinase (CSK), megakaryocyte-associated tyrosine-protein kinase (CTK), tyrosine-protein kinase receptor (EPH), Ephrin type-A receptor 1, Ephrin type-A receptor 4 (EPHA4), Ephrin type-B receptor 3 (EPHB3), Ephrin type-A receptor 8 (EPHA8), neurotrophic tyrosine kinase receptor, type 1 (NTRK1), protein-tyrosine kinase (PTK2), syk-related tyrosine kinase (SRK), protein tyrosine kinase (CTK), tyro3 protein tyrosine kinase (TYRO3), bruton agammaglobulinemia tyrosine kinase (BTK), leukocyte tyrosine kinase (LTK), protein-tyrosine kinase (SYK), protein-tyrosine kinase (STY), tek tyrosine kinase (TEK), elk-related tyrosine kinase (ERK), tyrosine kinase with immunoglobulin and egf factor homology domains (TIE), protein tyrosine kinase (TKF), neurotrophic tyrosine kinase, receptor, type 3 (NTRK3), mixed-lineage protein kinase-3 (MLK3), protein kinase, mitogen-activated 4 (PRKM4), protein kinase, mitogen-activated 1 (PRKM1), protein tyrosine kinase (PTK7), protein tyrosine kinase (EEK), minibrain (drosophila) homolog (MNBH), bone marrow kinase, x-linked (BMX), eph-like tyrosine kinase 1 (ETK1), macrophage stimulating 1 receptor (MST1R), btk-associated protein, 135 kd, lymphocyte-specific protein tyrosine kinase (LCK), fibroblast growth factor receptor-2 (FGFR2), protein tyrosine kinase-3 (TYK3), protein tyrosine kinase (TXK), tec protein tyrosine kinase (TEC), protein tyrosine kinase-2 (TYK2), eph-related receptor tyrosine kinase ligand 1 (EPLG1), t-cell tyrosine kinase (EMT), eph tyrosine kinase 1 (EPHT1), zona pellucida receptor tyrosine kinase, 95 kd (ZRK), protein kinase, mitogen-activated, kinase 1 (PRKMK1), eph tyrosine kinase 3 (EPHT3), growth arrest-specific gene-6 (GAS6), kinase insert domain receptor (KDR), axl receptor tyrosine kinase (AXL), fibroblast growth factor receptor-1 (FGFR1), v-erb-b2 avian erythroblastic leukemia viral oncogene homolog 2 (ERBB2), fms-like tyrosine kinase-3 (FLT3), neuroepithelial tyrosine kinase (NEP), neurotrophic tyrosine kinase receptor-related 3 (NTRKR3), eph-related receptor tyrosine kinase ligand 5 (EPLG5), neurotrophic tyrosine kinase, receptor, type 2 (NTRK2), receptor-like tyrosine kinase (RYK), tyrosine kinase, b-lymphocyte specific (BLK), eph tyrosine kinase 2 (EPHT2), eph-related receptor tyrosine kinase ligand 2 (EPLG2), glycogen storage disease VIII, eph-related receptor tyrosine kinase ligand 7 (EPLG7), janus kinase 1 (JAK1), fms-related tyrosine kinase-1 (FLT1), protein kinase, camp-dependent, regulatory, type I, alpha (PRKAR1A), wee-1 tyrosine kinase (WEE1), eph-like tyrosine kinase 2 (ETK2), receptor tyrosine kinase musk, insulin receptor (INSR), janus kinase 3 (JAK3), fms-related tyrosine kinase-3 ligand protein kinase c, beta 1 (PRKCB1), tyrosine kinase-type cell surface receptor (HER3), janus kinase 2 (JAK2), lim domain kinase 1 (LIMK1), dual specificity phosphatase 1 (DUSP1), hemopoietic cell kinase (HCK), tyrosine 3-monooxygenase/tryptophan 5-monooxygenase activation protein, eta polypeptide (YWHAH), ret proto-oncogene (RET), tyrosine 3-monooxygenase/tryptophan 5-monooxygenase activation protein, zeta polypeptide (YWHAZ), tyrosine 3-monooxygenase/tryptophan 5-monooxygenase activation protein, beta polypeptide (YWHAB), hepatoma transmembrane kinase (HTK), map kinase 6, phosphatidylinositol 3-kinase, catalytic, alpha polypeptide (PIK3CA), cyclin-dependent kinase inhibitor 3 (CDKN3), diacylglycerol kinase, delta, 130 kd, protein-tyrosine phosphatase, nonreceptor type, 13 (PTPN13), abelson murine leukemia viral oncogene homolog 1 (ABL1), diacylglycerol kinase, alpha (DAGK1), focal adhesion kinase 2, epithelial discoidin domain receptor 1 (EDDR1), anaplastic lymphoma kinase (ALK), phosphatidylinositol 3-kinase, catalytic, gamma polypeptide (PIK3CG), phosphatidylinositol 3-kinase regulatory subunit, (PIK3R1), eph homology kinase-1 (EHK1), v-kit hardy-zuckerman 4 feline sarcoma viral oncogene homolog (KIT), fibroblast growth factor receptor-3 (FGFR3), vascular endothelial growth factor c (VEGFC), epidermal growth factor receptor (EGFR), oncogene (TRK), growth factor receptor-bound protein-7 (GRB7), ras p21 protein activator (RAS2), met proto-oncogene (MET), src-like adapter (SLA), vascular endothelial growth factor (VEGF), vascular endothelial growth factor receptor (VEGFR), nerve growth factor receptor (NGFR), platelet derived growth factor receptor (PDGFR), platelet derived growth factor receptor beta (PDGFRB), dual-specificity tyrosine-(Y)-phosphorylation regulated kinase 2 (DYRK2), dual-specificity tyrosine-(Y)-phosphorylation regulated kinase 3 (DYRK3), dual-specificity tyrosine-(Y)-phosphorylation regulated kinase 4 (DYRK4), dual-specificity tyrosine-(Y)-phosphorylation regulated kinase 1A (DYRK1A), dual-specificity tyrosine-(Y)-phosphorylation regulated kinase 1B (DYRK1B), CDC-like kinase 1 (CLK1), protein tyrosine kinase STY, CDC-like kinase 4 (CLK4), CDC-like kinase 2 (CLK2) or CDC-like kinase 3 (CLK3).

In another embodiment, provided herein are methods for the treatment or prevention of a disease or disorder associated with the modulation, for example inhibition, of serine/threonine kinases or related molecules, including, but not limited to, cyclin-dependent kinase 7 (CDK7), rac serine/threonine protein kinase, serine-threonine protein kinase n (PKN), serine/threonine protein kinase 2 (STK2), zipper protein kinase (ZPK), protein-tyrosine kinase (STY), bruton agammaglobulinemia tyrosine kinase (BTK), mkn28 kinase, protein kinase, x-linked (PRKX), elk-related tyrosine kinase (ERK), ribosomal protein s6 kinase, 90 kd, polypeptide 3 (RPS6KA3), glycogen storage disease VIII, death-associated protein kinase 1 (DAPK1), pctaire protein kinase 1 (PCTK1), protein kinase, interferon-inducible double-stranded rna (PRKR), activin a receptor, type II-like kinase 1 (ACVRLK1), protein kinase, camp-dependent, catalytic, alpha (PRKACA), protein kinase, y-linked (PRKY), G protein-coupled receptor kinase 2 (GPRK21), protein kinase c, theta form (PRKCQ), lim domain kinase 1 (LIMK1), phosphoglycerate kinase 1 PGK1), lim domain kinase 2 (LIMK2), c-jun kinase, activin a receptor, type II-like kinase 2 (ACVRLK2), janus kinase 1 (JAK1), elk1 motif kinase (EMK1), male germ cell-associated kinase (MAK), casein kinase 2, alpha-prime subunit (CSNK2A2), casein kinase 2, beta polypeptide (CSNK2B), casein kinase 2, alpha 1 polypeptide (CSNK2A1), ret proto-oncogene (RET), hematopoietic progenitor kinase 1, conserved helix-loop-helix ubiquitous kinase (CHUK), casein kinase 1, delta (CSNK1D), casein kinase 1, epsilon (CSNK1E), v-akt murine thymoma viral oncogene homolog 1 (AKT1), tumor protein p53 (TP53), protein phosphatase 1, regulatory (inhibitor) subunit 2 (PPP1R2), oncogene pim-1 (PIM1), transforming growth factor-beta receptor, type II (TGFBR2), transforming growth factor-beta receptor, type I (TGFBR1), v-raf murine sarcoma viral oncogene homolog b1 (BRAF), bone morphogenetic receptor type II (BMPR2), v-raf murine sarcoma 3611 viral oncogene homolog 1 (ARAF1), v-raf murine sarcoma 3611 viral oncogene homolog 2 (ARAF2), protein kinase C (PKC), v-kit hardy-zuckerman 4 feline sarcoma viral oncogene homolog (KIT) or c-KIT receptor (KITR).

In another embodiment, provided herein are methods for the treatment or prevention of a disease or disorder associated with the modulation, for example inhibition, of a MAP kinase, including, but not limited to, mitogen-activated protein kinase 3 (MAPK3), p44erk1, p44mapk, mitogen-activated protein kinase 3 (MAP kinase 3; p44), ERK1, PRKM3, P44ERK1, P44MAPK, mitogen-activated protein kinase 1 (MAPK1), mitogen-activated protein kinase 1 (MEK1), MAP2K1 protein tyrosine kinase ERK2, mitogen-activated protein kinase 2, extracellular signal-regulated kinase 2, protein tyrosine kinase ERK2, mitogen-activated protein kinase 2, extracellular signal-regulated kinase 2, ERK, p38, p40, p41, ERK2, ERT1, MAPK2, PRKM1, PRKM2, P42MAPK, p41mapk, mitogen-activated protein kinase 7 (MAPK7), BMK1 kinase, extracellular-signal-regulated kinase 5, BMK1, ERK4, ERK5, PRKM7, nemo-like kinase (NLK), likely ortholog of mouse nemo like kinase, mitogen-activated protein kinase 8 (MAPK8), protein kinase JNK1, JNK1 beta protein kinase, JNK1 alpha protein kinase, c-Jun N-terminal kinase 1, stress-activated protein kinase JNK1, JNK, JNK1, PRKM8, SAPK1, JNK1, JNK21B1/2, mitogen-activated protein kinase 10 (MAPK10), c-Jun kinase 3, JNK3 alpha protein kinase, c-Jun N-terminal kinase 3, stress activated protein kinase JNK3, stress activated protein kinase beta, mitogen-activated protein kinase 9 (MAPK9), MAP kinase 9, c-Jun kinase 2, c-Jun N-terminal kinase 2, stress-activated protein kinase JNK2, JNK2, JNK2A, JNK2B, PRKM9, JNK-55, JNK2BETA, p54aSAPK, JNK2ALPHA, mitogen-activated protein kinase 14 (MAPK14), p38 MAP kinase, MAP kinase Mxi2, Csaids binding protein, MAX-interacting protein 2, stress-activated protein kinase 2A, p38 mitogen activated protein kinase, cytokine suppressive anti-inflammatory drug binding protein, RK, p38, EXIP, Mxi2, CSBP1, CSBP2, CSPB1, PRKM14, PRKM15, SAPK2A, p38ALPHA, mitogen-activated protein kinase 11 (MAPK11), stress-activated protein kinase-2, stress-activated protein kinase-2b, mitogen-activated protein kinase p38-2, mitogen-activated protein kinase p38beta, P38B, SAPK2, p38-2, PRKM11, SAPK2B, p38Beta, P38BETA2, mitogen-activated protein kinase 13 (MAPK13), stress-activated protein kinase 4, mitogen-activated protein kinase p38 delta, SAPK4, PRKM13, p38delta, mitogen-activated protein kinase 12 (MAPK12), p38gamma, stress-activated protein kinase 3, mitogen-activated protein kinase 3, ERK3, ERK6, SAPK3, PRKM12, SAPK-3, P38GAMMA, mitogen-activated protein kinase 6 (MAPK6), MAP kinase isoform p97, mitogen-activated 5 protein kinase, mitogen-activated 6 protein kinase, extracellular signal-regulated kinase 3, extracellular signal-regulated kinase, p97, ERK3, PRKM6, p97MAPK, mitogen-activated protein kinase 4 (MAPK4), Erk3-related protein kinase, mitogen-activated 4 protein kinase (MAP kinase 4; p63), PRKM4, p63MAPK, ERK3-RELATED or Extracellular signal-regulated kinase 8 (ERK7).

More particularly, cancers and related disorders that can be treated or prevented by methods and compositions provided herein include but are not limited to the following: Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome (or a symptom thereof such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia and chronic myelomonocytic leukemia (CMML), chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., *Medicine*, (1985), 2d ed., J.B. Lippincott Co., Philadelphia; and Murphy et al., *Informed Decisions: The Complete Book of Cancer Diagnosis, Treatment, and Recovery*, (1997), Viking Penguin, Penguin Books U.S.A., Inc., United States of America).

Accordingly, the methods and compositions provided herein are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal orignin, including fibrosarcoma and rhabdomyoscarcoma; other tumors, including melanoma, seminoma, tetratocarcinoma, neuroblastoma and glioma; tumors of the central and peripheral nervous system, including astrocytoma, glioblastoma multiforme, neuroblastoma, glioma, and schwannomas; solid and blood born tumors; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions disclosed herein. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the ovary, bladder, breast, colon, lung, skin, pancreas, or uterus. In other specific embodiments, sarcoma, melanoma, or leukemia is treated or prevented.

In another embodiment, the methods and compositions provided herein are also useful for administration to patients in need of a bone marrow transplant to treat a malignant disease (e.g., patients suffering from acute lymphocytic leukemia, acute myelogenous leukemia, chronic myelogenous leukemia, chronic lymphocytic leukemia, myelodysplastic syndrome ("preleukemia"), monosomy 7 syndrome, non-Hodgkin's lymphoma, neuroblastoma, brain tumors, multiple myeloma, testicular germ cell tumors, breast cancer, lung cancer, ovarian cancer, melanoma, glioma, sarcoma or other solid tumors), those in need of a bone marrow transplant to treat a non-malignant disease (e.g., patients suffering from hematologic disorders, congenital immunodeficiencies, mucopolysaccharidoses, lipidoses, osteoporosis, Langerhan's cell histiocytosis, Lesch-Nyhan syndrome or glycogen storage diseases), those undergoing chemotherapy or radiation therapy, those preparing to undergo chemotherapy or radiation therapy and those who have previously undergone chemotherapy or radiation therapy.

In another embodiment, provided herein are methods for the treatment of myeloproliferative disorders or myelodysplastic syndromes, comprising administering to a patient in need thereof an effective amount of a solid form comprising Compound I or a composition thereof. In certain embodiments, the myeloproliferative disorder is polycythemia rubra vera; primary thrombocythemia; chronic myelogenous leukemia; acute or chronic granulocytic leukemia; acute or chronic myelomonocytic leukemia; myelofibro-erythroleukemia; or agnogenic myeloid metaplasia.

In another embodiment, provided herein are methods for the treatment of cancer or tumors resistant to other kinase inhibitors such as imatinib mesylate (STI-571 or Gleevec™) treatment, comprising administering to a patient in need thereof an effective amount of a solid form comprising Compound I or a composition thereof. In a particular embodiment, provided herein are methods for the treatment of leukemias, including, but not limited to, gastrointestinal stromal tumor (GIST), acute lymphocytic leukemia or chronic myelocytic leukemia resistant to imatinib mesylate (STI-571 or Gleevec™) treatment, comprising administering to a patient in need thereof an effective amount of a solid form comprising Compound I or a composition thereof.

In one embodiment, provided herein are methods for treating or preventing a disease or disorder treatable or preventable by modulating a kinase pathway, in one embodiment, the JNK pathway, comprising administering an effective amount of a solid form comprising Compound I to a patient in need of the treating or preventing. Particular diseases which are treatable or preventable by modulating, for example, inhibiting, a kinase pathway, in one embodiment, the JNK pathway, include, but are not limited to, rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; Type II diabetes; obesity; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases; solid tumor; and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

Compound I can be combined with other pharmacologically active compounds ("second active agents") in methods and compositions described herein. It is believed that certain combinations may work synergistically in the treatment of particular types diseases or disorders, and conditions and symptoms associated with such diseases or disorders. Compound I can also work to alleviate adverse effects associated with certain second active agents, and vice versa.

One or more second active ingredients or agents can be used in the methods and compositions described herein. Second active agents can be large molecules (e.g., proteins) or small molecules (e.g., synthetic inorganic, organometallic, or organic molecules).

Examples of large molecule second active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); PI3K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, small molecule anti-cancer agents and antibiotics (e.g., clarithromycin).

Specific second active compounds that can be combined with Compound I vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BC ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clathromycin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in mutiple myeloma cells (such as, for example, TRAIL), bortezomib, statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

Similarly, examples of specific second active agents according to the indications to be treated, prevented, or managed can be found in the following references, all of which are incorporated herein in their entireties: U.S. Pat. Nos. 6,281,230 and 5,635,517; U.S. application Ser. Nos. 10/411,649, 10/483,213, 10/411,656, 10/693,794, 10/699,154, and 10/981,189; and U.S. provisional application Nos. 60/554,923, 60/565,172, 60/626,975, 60/630,599, 60/631,870, and 60/533,862.

Examples of additional second active agents include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate (Aspirin®), celecoxib (Celebrex®), Enbrel®, ketamine, gabapentin (Neurontin®), phenyloin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), nefazodone (Serzone®), venlafaxine (Effexor®), trazodone (Desyrel®), bupropion (Wellbutrin®), mexiletine, nifedipine, propranolol, tramadol, lamotrigine, ziconotide, ketamine, dextromethorphan, benzodiazepines, baclofen, tizanidine and phenoxybenzamine.

Examples of additional second active agents include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2ÿ, pentoxifylline, tin etiopurpurin, motexafin lutetium, 9-fluoro-11, 21-dihydroxy-16,17-1-methylethylidinebis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O-Ac genistin, daidzein, daidzin, 6'-O-Mal daidzin, 6'-O-Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited above are incorporated herein in their entireties by reference.

Examples of additional second active agents include, but are not limited to, keratolytics, retinoids, α-hydroxy acids, antibiotics, collagen, botulinum toxin, interferon, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of additional second active agents include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandinI 2 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Clalis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of additional second active agents include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of additioanl second active agents include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stiboglucuronate), interfereon gamma, itraconazole, a combination of dead promastigotes and BCG, leucovorin, corticosteroids, sulfonamide, spiramycin, IgG (serology), trimethoprim, and sulfamethoxazole.

Examples of additional second active agents include, but are not limited to: antibiotics (therapeutic or prophylactic) such as, but not limited to, ampicillin, clarithromycin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-ÿ), antibodies (e.g., anti-CD40 and IgM), oligonucleotides containing unmethylated CpG motifs, and vaccines (e.g., viral and tumor peptide vaccines).

Examples of additional second active agents include, but are not limited to: a dopamine agonist or antagonist, such as, but not limited to, Levodopa, L-DOPA, cocaine, α-methyltyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and a mixture thereof.

Examples of additional second active agents include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises l-threo-methylphenidate, d-threo-methylphenidate, dl-threo-methylphenidate, l-erythro-methylphenidate, d-erythro-methylphenidate, dl-erythro-methylphenidate, and a mixture thereof; and a diuretic agent such as, but not limited to, mannitol, furosemide, glycerol, and urea.

Examples of additional second active agents include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of additional second active agents include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

Administration of Compound I and a second active agent to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. In certain embodiments, Compound I is administered orally. Preferred routes of administration for the second active agents or ingredients provided herein are known to those of ordinary skill in the art. See, e.g., *Physicians' Desk Reference,* 1755-1760 (56th ed., 2002).

In one embodiment, the second active agent is administered intravenously or subcutaneously. In another embodiment, the second active agent is administered intravenously or subcutaneously once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of Compound I and any optional additional active agents concurrently administered to the patient.

5.4 Pharmaceutical Compositions and Routes of Administration

The solid forms comprising Compound I can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the solid forms comprising Compound I in the pharmaceutical composition may be at a level that will exercise the desired effect; for example, about 0.005 mg/kg of a patient's body weight to about 10 mg/kg of a patient's body weight in unit dosage for both oral and parenteral administration.

The physical characteristics of different solid forms can, in some cases, affect their bioavailability, but the amounts of the solid forms that are therapeutically or prophylactically effective in the treatment of various diseases and conditions can be readily determined by those of ordinary skill in the pharmacy or medical arts. In general, the solid forms comprising Compound I can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment one dose is given per day. In any given case, the amount of the solid form comprising Compound I administered will depend on such factors as the solubility of the active component, the formulation used and the route of administration.

In another embodiment, provided herein are methods for the treatment or prevention of a disease or disorder comprising the administration of about 0.375 mg day to about 750 mg/day, about 0.75 mg/day to about 375 mg day, about 3.75 mg day to about 75 mg day, about 7.5 mg day to about 55 mg day or about 18 mg day to about 37 mg/day of a solid form comprising Compound I to a patient in need thereof.

In another embodiment, provided herein are methods for the treatment or prevention of a disease or disorder comprising the administration of about 1 mg day to about 1200 mg day, about 10 mg day to about 1200 mg/day, about 100 mg day to about 1200 mg day, about 400 mg day to about 1200 mg day, about 600 mg day to about 1200 mg day, about 400 mg/day to about 800 mg day or about 600 mg day to about 800 mg day of a solid form comprising Compound I to a patient in need thereof. In a particular embodiment, the methods disclosed herein comprise the administration of 400 mg day, 600 mg day or 800 mg day of a solid form comprising Compound I to a patient in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a solid form comprising Compound I.

In a particular embodiment, provided herein are unit dosage formulation comprising about 100 mg or 400 mg of a solid form comprising Compound I.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a solid form comprising Compound I.

A solid form comprising Compound I can be administered once, twice, three, four or more times daily. In a particular embodiment, doses of 600 mg or less are administered as a once daily dose and doses of more than 600 mg are administered twice daily in an amount equal to one half of the total daily dose.

A solid form comprising Compound I can be administered orally for reasons of convenience. In one embodiment, when administered orally, Compound I is administered with a meal and water. In another embodiment, the Compound I is dispersed in water or juice (e.g., apple juice or orange juice) and administered orally as a suspension.

The solid form comprising Compound I can also be administered intradermally, intramuscularly, intraperitoneally, percutaneously, intravenously, subcutaneously, intranasally, epidurally, sublingually, intracerebrally, intravaginally, transdermally, rectally, by inhalation, or topically to the ears, nose, eyes, or skin. The mode of administration is left to the discretion of the health-care practitioner, and can depend in-part upon the site of the medical condition.

In one embodiment, provided herein are capsules containing a solid form comprising Compound I without an additional carrier, excipient or vehicle.

In another embodiment, provided herein are compositions comprising an effective amount of a solid form comprising Compound I and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a solid form comprising Compound I with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a solid form comprising Compound I as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the solid form comprising Compound I can be delayed or prolonged by proper formulation. For example, a slowly soluble pellet of the solid form comprising Compound I can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the solid form comprising Compound I in oily or emulsified vehicles that allow it to disperse slowly in the serum.

6. EXAMPLES

The following Examples are presented by way of illustration, not limitation.

6.1 Example 1

Synthesis of 4-[9-(tetrahydro-furan-3-yl)-8-(2,4,6-trifluoro-phenylamino)-9H-purin-2-ylamino]-cyclohexan-1-ol The compound named 4-[9-(tetrahydro-furan-3-yl)-8-(2, 4,6-trifluoro-phenylamino)-9H-purin-2-ylamino]-cyclohexan-1-ol ("Compound I"), can be prepared using the synthesis outlined in FIG. 13. Starting from Compound A (2,4-dichloro-5-nitropyrimidine), Compound I is obtained in 40% overall yield and the purity is >99% (HPLC area percent). A total of 550 g of Compound I was prepared by this process.

Stages 1A & 1B involve a "one-pot" formation of Compound B (2,4-diamino-substituted-5-nitropyrimidine) via a sequential chemoselective displacement of the chloro groups with the appropriate amine. Compound A (2,4-dichloro-5-nitropyrimidine) (363 g, 1.87 mol, 1.0 eq.) was charged to a reaction vessel with (S)-3-amino tetrahydrofuran (1) (230 g, 1.87 mol, 1.0 eq.) and $CH_2Cl_2$ (DCM) (3.45 L, 15 vol.). The displacement of the 4-chloro group with (S)-3-amino tetrahydrofuran (1) in the presence of DIPEA (684 mL, 3.93 mol, 2.1 eq.) was performed at −30 to −20° C. followed by warming the reaction to 20-25° C. over 10-18 h. Upon consumption of Compound A (IPC indicated <1 AP, HPLC) the reaction mixture was charged with trans-4-amino cyclohexanol (3) (215 g, 1.87 mol, 1.0 eq.) and additional DIPEA (391 mL, 2.24 mol, 1.2 eq.). The mixture was heated at 35-40° C. for 10-18 h or until HPLC analysis indicated <1 AP, (HPLC) of 2. A solvent swap of DCM to MeCN was carried out by distilling off about 12 volumes of DCM and adding about 3 volumes of MeCN. Water (4.6 L, 20 vol) was then added and the reaction mixture was cooled to between about 0-5° C. and stirred for about 1-2 h to give Compound B as a filterable solid. The solids were collected by filtration, washed with water (2.3 L, 10 vol), washed with MTBE (2.3 L, 10 vol) and dried at 35-40° C. until KF<3% (yield 82-89 M %, HPLC purity 90-95 AP).

Stage 2A involves the reduction of the nitro group of Compound B to the corresponding aniline (4). A mixture of Compound B (120 g, 0.37 mol, 1.0 eq.) and 10% Pd/C (50% wet, 10 wt %) (12 g, 10 wt %) were charged with MeOH (1.5 L, 12.5 vol). The mixture was hydrogenated at 35-40° C., 40-50 psi $H_2$ for 2-4 h with shaking (or until HPLC analysis indicated <1 AP (HPLC) of Compound B remaining). The catalyst was removed by filtration through a celite bed. The celite was washed with warm (35-40° C.) MeOH (1.2 L, 10 vol). The filtrate was concentrated and a solvent swap of MeOH to THF was carried out by distilling off MeOH and charging with THF (1.8 L, 15 vol) to give a THF solution/slurry of Stage 2A product (4), which was carried to the next step (yield assumed >99 M %, HPLC purity>94 AP). The solvent swap with THF was performed until the $^1H$ NMR of the distillate revealed <2% of MeOH. The THF solution can be stored for up to 24 h at ambient temperature (20-25° C.) under $N_2$ without degradation.

Stage 2B involves the coupling of Stage 2A product (4) with commercially available 2,4,6-trifluorophenyl isothiocyanate (5). Stage 2A product (4) (217.7 g, 0.742 mol, 1 eq.) as a THF solution was reacted with 2,4,6-trifluorophenyl isothiocyanate (5) with stirring at 20-25° C. for 15-18 h (or until IPC indicated <1 AP (HPLC) of (4)) to afford the intermediate thiourea (6). The reaction was charged with EDC (156.5 g, 0.816 mol. 1.1 eq.) and heated at 60-65° C. for 3.5-6 h (or until IPC indicated <1 AP (HPLC) of (6)) to give the desired crude purine (Compound I). The mixture was then treated with AcOH/$H_2O$ (212 mL, 3.71 mol, 5 eq.) and water (650 mL, 3 vol) and heated for 1.5-2 h at 60-65° C. The mixture was then cooled to 20-25° C. and diluted with EtOAc (3.3 L, 15 vol). The phases were separated and the organic phase was washed with water (2×5 vol), $Na_2CO_3$ (2×5 vol. 5 eq.) (or until pH=9-11) and again with water (5 vol). The organic phase (EtOAc) was collected and water was removed by azeotropic distillation using EtOAc) until KF<5%. A solvent swap with EtOH was performed by distilling off EtOAc and charging with EtOH (1.1 L, 5 vol) until the $^1H$ NMR of the distillate revealed <2% of EtOAc. The ethanol slurry of crude Compound I can be stored for up to 64 h at 20-25° C. under an inert atmosphere. The resultant slurry was then heated to 78-83° C. and water (15 volumes) was added at such a rate as to maintain the reaction temperature at >75° C. The solution was seeded (1-2 wt % Compound I), followed by the addition of water (5 volumes) and cooling of the reaction mixture to 20-25° C. Crude Compound I was collected by filtration and dried in vacuo at 35-40° C. for 18-24 h (or until KF<1%) (yield 55-62 M %, HPLC purity 88-99 AP).

Stage 3 involves recrystallization of crude Compound I. Crude Compound I (717 g, 1.0 eq.) was heated in EtOH (6.1 L, 8.5 vol) at 78-83° C. and stirred until solids dissolved. The solution of crude Compound I was cooled to 50-55° C. and polish filtered. The solution was then heated to 78-83° C. and water (10.8 L, 15 volumes) was added while maintaining the temperature at >75° C. The solution was seeded (7 g, 1-2 wt % Compound I), followed by cooling of the reaction mixture to 20-25° C. Recrystallized Compound I was collected by filtration and dried at up to 40° C. (or until KF<1%) (recovery 78-80 M %, HPLC purity 99.42 AP).

Compound I was also prepared according to the alternative methods depicted in FIG. 15 and FIG. 16.

6.2 Example 2

Preparation of Solid Forms

General Procedures

Equilibration slurry and evaporation experiments were carried out by adding an excess of Compound I free base or HCl salt to 2 mL of solvent. The resulting mixture was agitated for at least 24 hours at 25° C. and 50° C. in two separate sets of experiments. Upon reaching equilibrium, the saturated supernatant solution was removed and allowed to evaporate slowly in an open vial under nitrogen at 25° C. or 50° C., respectively. The slurry resulting from the equilibration was filtered and air-dried.

Crystallization using cooling methods were performed for Compound I free base. Compound I was dissolved in a solvent at an elevated temperature, approximately 65° C., and allowed to cool to ambient temperature. Samples that did not crystallize at ambient temperature were placed in a refrigerator (about 2-8° C.). Solids were isolated by decantation and allowed to dry in the air.

Precipitations for Compound I free base were also carried out using solvent/antisolvent combinations. The solid was dissolved in a solvent in Compound I had high solubility, and then a selected solvent in which Compound I was relatively insoluble (i.e., an antisolvent) was added to the solution. A precipitate was formed immediately in some solvent/antisolvent systems. If precipitation did not immediately occur, the resulting mixture was allowed to cool in a refrigerator until a precipitate formed. The precipitate was then isolated by decantation and allowed to dry in the air.

Results of Compound I Free Base Crystallization Experiments

| Solvent | Condition | Resulting Form by XRPD |
|---|---|---|
| Acetone | Evaporation at about 25° C. | Compound I Free Base Form A |
| n-Butanol | Evaporation at about 25° C. | Compound I Free Base Form A |
| Absolute ethanol | Evaporation at about 25° C. | Compound I Free Base Form A |
| Methanol | Evaporation at about 25° C. | Compound I Free Base Form A |
| 2-Propanol | Evaporation at about 25° C. | Compound I Free Base Form A |
| Tetrahydrofuran | Evaporation at about 25° C. | Compound I Free Base Form A |
| Ethanol/Water (1/1) | Evaporation at about 25° C. | Compound I Free Base Form A |
| Acetone | Evaporation at about 50° C. | Compound I Free Base Form A |
| n-Butanol | Evaporation at about 50° C. | Compound I Free Base Form A |
| Absolute ethanol | Evaporation at about 50° C. | Compound I Free Base Form A |
| Methanol | Evaporation at about 50° C. | Compound I Free Base Form A |
| 2-Propanol | Evaporation at about 50° C. | Compound I Free Base Form A |
| Tetrahydrofuran | Evaporation at about 50° C. | Compound I Free Base Form A |
| Ethanol/Water (1/1) | Evaporation at about 50° C. | Compound I Free Base Form A |
| Acetone | Slurry at about 25° C. | Compound I Free Base Form A |
| Acetonitrile | Slurry at about 25° C. | Compound I Free Base Form A |
| n-Butanol | Slurry at about 25° C. | Compound I Free Base Form A |
| Ethanol | Slurry at about 25° C. | Compound I Free Base Form A |
| Ethyl acetate | Slurry at about 25° C. | Compound I Free Base Form A |
| Heptane | Slurry at about 25° C. | Compound I Free Base Form A |
| Methylene chloride | Slurry at about 25° C. | Compound I Free Base Form A |
| Methyl ethyl ketone | Slurry at about 25° C. | Compound I Free Base Form A |
| Methyl t-butyl ether | Slurry at about 25° C. | Compound I Free Base Form A |
| 2-Propanol | Slurry at about 25° C. | Compound I Free Base Form A |
| Toluene | Slurry at about 25° C. | Compound I Free Base Form A |
| Water | Slurry at about 25° C. | Compound I Free Base Form A |
| Ethanol/Water (1/1) | Slurry at about 25° C. | Compound I Free Base Form A |
| Acetone | Slurry at about 50° C. | Compound I Free Base Form A |
| Acetonitrile | Slurry at about 50° C. | Compound I Free Base Form A |
| n-Butanol | Slurry at about 50° C. | Compound I Free Base Form A |
| Ethanol | Slurry at about 50° C. | Compound I Free Base Form A |
| Ethyl acetate | Slurry at about 50° C. | Compound I Free Base Form A |
| Heptane | Slurry at about 50° C. | Compound I Free Base Form A |
| Methyl ethyl ketone | Slurry at about 50° C. | Compound I Free Base Form A |
| 2-Propanol | Slurry at about 50° C. | Compound I Free Base Form A |
| Toluene | Slurry at about 50° C. | Compound I Free Base Form A |
| Water | Slurry at about 50° C. | Compound I Free Base Form A |
| Ethanol/Water (1/1) | Slurry at about 50° C. | Compound I Free Base Form A |

Results of Compound I Free Base Crystallization
Experiments, continued

| Solvent | Condition | Resulting Form by XRPD |
|---|---|---|
| Ethanol | Antisolvent precipitation with MTBE (1:10 solvent:antisolvent ratio at 50° C.) | Compound I Free Base Form A |
| Ethanol | Antisolvent precipitation with heptane (1:10 solvent:antisolvent ratio at 50° C.) | Compound I Free Base Form A |
| THF | Antisolvent precipitation with MTBE (1:10 solvent:antisolvent ratio at 50° C.) | Compound I Free Base Form A |
| THF | Antisolvent precipitation with heptane (1:10 solvent:antisolvent ratio at 50° C.) | Compound I Free Base Form A |
| THF | Antisolvent precipitation with toluene (1:10 solvent:antisolvent ratio at 50° C.) | Compound I Free Base Form A |
| Acetone | Equilibrate Form A in solvent for 4 weeks at 40° C. | Compound I Free Base Form A |
| Acetonitrile | Equilibrate Form A in solvent for 4 weeks at 40° C. | Compound I Free Base Form A |
| Ethyl acetate | Equilibrate Form A in solvent for 4 weeks at 40° C. | Compound I Free Base Form A |
| Heptane | Equilibrate Form A in solvent for 4 weeks at 40° C. | Compound I Free Base Form A |
| 2-Propanol | Equilibrate Form A in solvent for 4 weeks at 40° C. | Compound I Free Base Form A |
| MTBE | Equilibrate Form A in solvent for 4 weeks at 40° C. | Compound I Free Base Form A |
| Toluene | Equilibrate Form A in solvent for 4 weeks at 40° C. | Compound I Free Base Form A |
| Water | Equilibrate Form A in solvent for 4 weeks at 40° C. | Compound I Free Base Form A |
| Ethanol/water (1/1) | Slow cooling crystallization | Compound I Free Base Hydrate |

Results of Compound I HCl Salt Crystallization
Experiments

| Solvent | Condition | Resulting Form by XRPD |
|---|---|---|
| n-Butanol | Evaporation at about 25° C. | Compound I HCl Salt Form A |
| Absolute ethanol | Evaporation at about 25° C. | Compound I HCl Salt Form A |
| Methanol | Evaporation at about 25° C. | Compound I HCl Salt Form A |
| 2-Propanol | Evaporation at about 25° C. | Compound I HCl Salt Form A |
| Water | Evaporation at about 25° C. | Compound I HCl Salt Form A |
| Ethanol/Water (1/1) | Evaporation at about 25° C. | Compound I HCl Salt Form A |
| n-Butanol | Evaporation at about 25° C. | Compound I HCl Salt Form A |
| Absolute ethanol | Evaporation at about 25° C. | Compound I HCl Salt Form A |
| Methanol | Evaporation at about 25° C. | Compound I HCl Salt Form A + amorphous |
| 2-Propanol | Evaporation at about 25° C. | Compound I HCl Salt Form A |
| Water | Evaporation at about 25° C. | Compound I HCl Salt amorphous |
| Ethanol/Water (1/1) | Evaporation at about 25° C. | Compound I HCl Salt amorphous |
| Acetone | Slurry at about 25° C. | Compound I HCl Salt Form A |
| Acetonitrile | Slurry at about 25° C. | Compound I HCl Salt Form A |
| n-Butanol | Slurry at about 25° C. | Compound I HCl Salt Form A |
| Ethyl acetate | Slurry at about 25° C. | Compound I HCl Salt Form A |
| Heptane | Slurry at about 25° C. | Compound I HCl Salt Form A |
| Methylene chloride | Slurry at about 25° C. | Compound I HCl Salt Form A |
| Methyl ethyl ketone | Slurry at about 25° C. | Compound I HCl Salt Form A |
| Methyl t-butyl ether | Slurry at about 25° C. | Compound I HCl Salt Form A |
| 2-Propanol | Slurry at about 25° C. | Compound I HCl Salt Form A |
| Toluene | Slurry at about 25° C. | Compound I HCl Salt Form A |
| Tetrahydrofuran | Slurry at about 25° C. | Compound I HCl Salt Form A |
| Acetone | Slurry at about 50° C. | Compound I HCl Salt Form A |
| Acetonitrile | Slurry at about 50° C. | Compound I HCl Salt Form A |
| n-Butanol | Slurry at about 50° C. | Compound I HCl Salt Form A |
| Ethyl acetate | Slurry at about 50° C. | Compound I HCl Salt Form A |
| Heptane | Slurry at about 50° C. | Compound I HCl Salt Form A |
| Methyl ethyl ketone | Slurry at about 50° C. | Compound I HCl Salt Form A |

| Solvent | Condition | Resulting Form by XRPD |
|---|---|---|
| 2-Propanol | Slurry at about 50° C. | Compound I HCl Salt Form A |
| Toluene | Slurry at about 50° C. | Compound I HCl Salt Form A |
| Tetrahydrofuran | Slurry at about 50° C. | Compound I HCl Salt Form A |
| Acetone | Equilibrate HCl salt in solvent for 4 weeks at 40° C. | Compound I HCl Salt Form A |
| Acetonitrile | Equilibrate Form A in solvent for 4 weeks at 40° C. | Compound I HCl Salt Form A |
| Ethyl acetate | Equilibrate Form A in solvent for 4 weeks at 40° C. | Compound I HCl Salt Form A |
| Heptane | Equilibrate Form A in solvent for 4 weeks at 40° C. | Compound I HCl Salt Form A |
| 2-Propanol | Equilibrate Form A in solvent for 4 weeks at 40° C. | Compound I HCl Salt Form A |
| MTBE | Equilibrate Form A in solvent for 4 weeks at 40° C. | Compound I HCl Salt Form A |
| Toluene | Equilibrate Form A in solvent for 4 weeks at 40° C. | Compound I HCl Salt Form A |
| THF | Equilibrate Form A in solvent for 4 weeks at 40° C. | Compound I HCl Salt Form A |

6.3 Example 3

Approximate Solubilities of Solid Forms

A weighed sample comprising either the free base or the HCl salt of Compound I was treated with 2 mL of a solvent (either HPLC or reagent grade). The resulting mixture was agitated for at least 24 hours at about 25° C. When all of the solids were dissolved by visual inspection, the estimated solubility was calculated. The solubility was estimated from these experiments based on the total volume of solvent used to give a complete solution. Measured values are provided in the tables below. The actual solubility may be greater than those calculated due to the use of a large amount of solvent or a slow rate of dissolution. A known volume of filtrate was evaporated to dryness and the weight of the residue was measured.

Approximate Solubilities of Solid Form Comprising Compound I

| Solvent | Approximate Solubility (mg/mL) of Form A of the Free Base of Compound I | Approximate Solubility (mg/mL) of Form A of the Free Base of Compound I |
|---|---|---|
| Acetone | 11.58 | 1.14 |
| Acetonitrile | 2.58 | 1.56 |
| n-Butanol | 19.31 | 7.50 |
| Absolute ethanol | 47.09 | >50 |
| Ethyl acetate | 3.91 | 0.02 |
| Heptane | 0.55 | 0.51 |
| Methylene chloride | 11.57 | 5.00 |
| Methyl ethyl ketone | 8.74 | 0.68 |
| Methanol | >50 | >50 |
| Methyl t-butyl ether | 1.10 | 0.46 |
| 2-Propanol | 15.65 | 6.39 |
| Tetrahydrofuran | >50 | 2.03 |
| Toluene | 0.36 | 0.04 |
| Water | 0.41 | >50 |
| Ethanol/Water (1/1) | 11.63 | >50 |

6.4 Example 4

Preparation of Form A of the Free Base of Compound I

Crude 4-[9-(tetrahydro-furan-3-yl)-8-(2,4,6-trifluoro-phenylamino)-9H-purin-2-ylamino]-cyclohexan-1-ol ("Compound I") (5 g) was dissolved in ethanol (35 ml, 7 vol) at reflux (78-82° C.). Water (75 ml, 15 vol) was added, maintaining the temperature above 75° C. The solution was seeded (0.5-1%) and allowed to cool to ambient temperature (20-25° C.) over 4-6 h. The product was collected by filtration and washed with water (25 ml, 5 vol) then dried (18 h, 40-45° C.) to yield Form A of the free base of Compound I as an off-white crystalline solid. Form A is the imine tautomer of 4-[9-(terahydro-furan-3-yl)-8-(2,4,6-trifluoro-phenylamino)-9H-purin-2-ylamino]-cyclonhexan-1-ol having the structure:

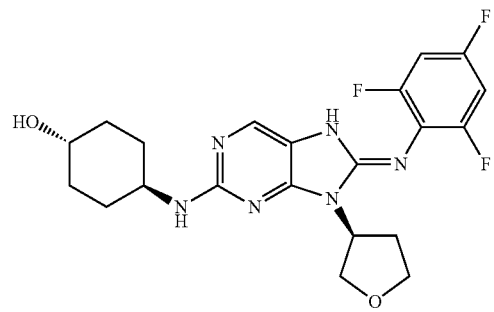

6.5 Example 5

Preparation of a Hydrate of the Free Base of Compound I

Crude 4-[9-(tetrahydro-furan-3-yl)-8-(2,4,6-trifluoro-phenylamino)-9H-purin-2-ylamino]-cyclohexan-1-ol ("Compound I") (100 mg) was dissolved in a 1:1 mixture of ethanol and water (2 mL) at approximately 65° C. The solution was cooled slowly to about 4° C. Resulting solids were isolated by decanting the liquid, and the solids were allowed to air dry. The resulting white solid was characterized by XRPD, DSC and TG/IR as a crystalline hydrate of the free base of Compound I. By microscopy, the solid comprised needle-shaped crystals.

6.6 Example 6

Preparation of Form A of the HCl Salt of Compound I

Form A of the bis-HCl salt of Compound I can be prepared by the two procedures described below.

Procedure 1: To a sample (100-200 mg) of the free base of Compound I was added solvent (15-30 volumes) and the mixture was heated (60-85° C.) until dissolution occurred. The solution was allowed to cool to room temperature (20-25° C.) and gaseous hydrochloric acid (1-3 eq) was added. The sample was stored between 5-25° C. and monitored for crystallization for up to 3 weeks. The Form A crystal form of the bis-HCl salt of Compound I that crystallized from this procedure was isolated by filtration, dried (20-40° C.) and analyzed.

Procedure 2: A 7.2 g batch of Form A the bis-HCl salt of Compound I was prepared from 8 g of the free base of Compound I. The free base of Compound I was dissolved in ethanol (9 volumes) at 75-80° C. The solution was allowed to cool to room temperature (20-25° C.), then concentrated (12 M aqueous) HCl (3 eq) was added. The solution was cooled to 0-5° C. for 2-4 h until crystallization was observed. The crystals of the Form A crystal form of the bis-HCl salt of Compound I were isolated by filtration, dried and analyzed.

6.7 Example 7

Preparation of Form A of the HBr Salt of Compound I

Form A of the HBr salt of Compound I was prepared by the procedure described below.

To a sample (100-200 mg) of the free base of Compound I was added solvent (15-30 volumes) and the mixture was heated (60-85° C.) until dissolution occurred. The solution was allowed to cool to room temperature (20-25° C.) and gaseous hydrobromic acid (1-3 eq) was added. The sample was stored between 5-25° C. and monitored for crystallization for up to 3 weeks. The Form A crystal form of the HBr salt of Compound I that crystallized from this procedure was isolated by filtration, dried (20-40° C.) and analyzed.

6.8 Example 8

Preparation of Form A of the Sulfate Salt of Compound I

Form A of the sulfate salt of Compound I was prepared by the procedures described below.

The free base of Compound I was dissolved in 15 volumes of ethanol at a temperature of 70-75° C. Following dissolution, excess sulfuric acid was added to the solution. Crystallization of Form A of the sulfate salt of Compound I was observed after 18 h.

The free base of Compound I was dissolved in 30 volumes of isopropanol at a temperature of 80-85° C. Following dissolution, excess sulfuric acid was added to the solution. Crystallization of Form A of the sulfate salt of Compound I was observed after 18 h.

6.9 Example 9

Analytical Methods 6.9.1 X-Ray Powder Diffraction

X-ray powder diffraction (XRPD) measurements were performed in accordance with United States Pharmacopeia (USP) monograph <941> entitled "X-ray Diffraction" (See, e.g., *The United States Pharmacopeia, The National Formulary*, 2003, The Unites States Pharmacopeial Convention, Inc., Rockville, Md., 2002, which is herein incorporated by reference in its entirety). A Thermo ARL X'TRA X-ray powder diffractometer (Thermo Electron Corp., Waltham, Mass.), equipped with Nickel-filtered Cu Kα radiation at 1.54 Å, was used for XRPD measurements from about 1.5 °2θ to about 40 °2θ, with a step size of about 0.020°, a count time of about 0.50 seconds per step, and a step scan rate of about 2.40°/min. The instrument was equipped with a fine focus X-ray tube. The voltage and amperage were set at 45 kV and 40 mA, respectively. The divergence slits were set at 0.5 mm and 0.2 mm. Diffracted radiation was measured using a Peltier-cooled Si (Li) solid-state detector. Representative XRPD patterns were presented displaying intensity (counts per second) versus position (°2θ). A sintered alumina standard was used to check peak positions. Peak positions may vary from sample to sample by approximately ±0.1 °2θ. Variation in peak position may depend upon multiple factors, including particle size, sample preparation, data collection temperature and parameters. Variation in peak intensity may occur, e.g., as a result of preferred orientation and/or variation in crystal habit.

6.9.2 Thermal Analysis

Differential scanning calorimetry (DSC) measurements were performed in accordance with United States Pharmacopeia (USP) monograph <891> entitled "Thermal nalysis" (See, e.g., *The United States Pharmacopeia, The National Formulary*, 2003, The Unites States Pharmacopeial Convention, Inc., Rockville, Md., 2002, which is incorporated herein by reference in its entirety). A DSC model Q1000 (TA Instruments, New Castle, Del.) was used to obtain DSC measurements. Indium was used as the calibration standard. Analysis was performed on accurately weighed samples with masses ranging between about 2 mg and about 5 mg. Samples were heated under nitrogen from about 25° C. to about 300° C. at a constant heating rate of about 10° C./min. Representative DSC thermograms were presented displaying heat flow (W/g) versus temperature (° C.). Melting points were reported as extrapolated onset temperatures.

Thermal gravimetric analysis (TGA) measurements were performed in accordance with United States Pharmacopeia (USP) monograph <891> entitled "Thermal nalysis" (See, e.g., *The United States Pharmacopeia, The National Formulary*, 2003, The Unites States Pharmacopeial Convention, Inc., Rockville, Md., 2002, which is incorporated herein by reference in its entirety). A TGA model Q500 (TA Instruments, New Castle, Del.) was used to obtain TGA measurements. Analysis was performed on samples with masses ranging between about 10.0 mg and about 50.0 mg. Samples were heated under nitrogen from about 25° C. to about 300° C. at a constant heating rate of about 10° C./min. Representative TGA thermograms were presented with one trace displaying weight (%) versus temperature (° C.), and a second trace displaying derivative weight (%/° C.) versus temperature (° C.).

6.9.3 Morphology Analysis

Morphology analysis of the samples was carried out using an Olympus optical microscope. The instrument was calibrated according to USP standards.

6.9.4 Moisture Sorption Analysis

Hygroscopicity (moisture sorption desorption) was determined by Dynamic Vapor Sorption (DVS). A solid sample comprising Compound I ranging from 10 to 50 mg was placed into the DVS instrument at 0% relative humidity (RH). The RH was increased from 0% to 80% or 95%. The RH was then decreased in a similar manner to accomplish a full sorption desorption cycle.

6.9.5 HPLC Analysis

HPLC methods for analysis of the purity of Compound I and/or its synthetic intermediates are provided as guidelines, and appropriate changes may be added to obtain comparable results. HPLC methods provided below correspond to the synthetic steps depicted in FIG. 13.

Stage 1A, In-Process: A sample of the reaction mixture (0.1 ml) was diluted with 10 ml of 1:1 $CH_3CN$:0.1% aq. $H_3PO_4$ and then analyzed using the following HPLC conditions. Column: Phenomenex HYPERSIL™ BDS C8 (4.6×250 mm), 5 µ, 120 A; Detection: 210, 240 nm, UV detector; Injection volume: 10.0µl; Temperature: 35° C.; Run time: 20 min; Mobile phase: A=$CH_3CN$, B=aq. 10 mmol $KH_2PO_4$, pH=3 ($H_3PO_4$); Flow: 1.00 ml/min; Gradient: 0 min=10.0% A+90.0% B, 20.00 min=70.0% A+30.0% B, 20.01 min=10.0% A+90.0% B. The reaction was considered complete when <0.1% (HPLC AP) of the starting material, Compound A, remained (approximate retention time of Compound A was 14.83 min).

Stage 1B, In-Process: A sample of the reaction mixture (0.1 ml) was diluted with 10 ml of 1:1 $CH_3CN$:0.1% aq. $H_3PO_4$ and then analyzed using the following HPLC conditions. Column: Phenomenex HYPERSIL™ BDS C8 (4.6×250 mm), 5 µ, 120 A; Detection: 210, 240 nm, UV detector; Injection volume: 10.0 µl; Temperature: 35° C.; Run time: 20 min; Mobile phase: A=$CH_3CN$, B=aq. 10 mmol $KH_2PO_4$, pH=3 ($H_3PO_4$); Flow: 1.00 ml/min; Gradient: 0 min=10.0% A+90.0% B, 20.00 min=70.0% A+30.0% B, 20.01 min=10.0% A+90.0% B. The reaction was considered complete when <0.1% (HPLC AP) of intermediate 2 remained (approximate retention time of 2 was 13.23 min).

Compound B, Purity: 50 mg of Compound B was dissolved and diluted with 100 ml of 1:1 $CH_3CN$:0.1% aq. $H_3PO_4$ and then analyzed using the following HPLC conditions. Column: Phenomenex HYPERSIL™ BDS C8 (4.6×250 mm), 5 µ, 120 A; Detection: 210, 240 nm, UV detector; Injection volume: 10.0 µl; Temperature: 35° C.; Run time: 30 min; Mobile phase: A=$CH_3CN$, B=aq. 10 mmol $KH_2PO_4$, pH=3 ($H_3PO_4$); Flow: 1.00 ml/min; Gradient: 0 min=10.0% A+90.0% B, 30.00 min=40.0% A+60.0% B, 30.01 min=10.0% A+90.0% B. The approximate retention time of Compound B was 18.92 min.

Stage 2A, In-Process: A sample of the reaction mixture (0.1 ml) was diluted with 10 ml of 1:1 $CH_3CN$:0.1% aq. $H_3PO_4$, filtered to remove the Pd catalyst, then analyzed using the following HPLC conditions. Column: Phenomenex HYPERSIL™ BDS C8 (4.6×250 mm), 5µ, 120 A; Detection: 210, 240 nm, UV detector; Injection volume: 10.0 µl; Temperature: 35° C.; Run time: 20 min; Mobile phase: A=$CH_3CN$, B=aq. 10 mmol $KH_2PO_4$, pH=3 ($H_3PO_4$); Flow: 1.00 ml/min; Gradient: 0 min=1.0% A+99.0% B, 10.00 min=60.0% A+40.0% B, 15.00 min=85.0% A+15.0% B, 16.00 min=85.0% A+15.0% B, 16.01 min=1.0% A+99.0% B. The reaction was considered complete when <1% (HPLC AP) of Compound B remained (approximate retention time of Compound B was 10.15 min).

Stage 2B, Synthesis of Intermediate 6, In-Process: A sample of the reaction mixture (0.1 ml) was diluted with 10 ml of 1:1 $CH_3CN$:0.1% aq. $H_3PO_4$ and then analyzed using the following HPLC conditions. Column: Phenomenex HYPERSIL™ BDS C8 (4.6×250 mm), 5 µ, 120 A; Detection: 210, 240 nm, UV detector; Injection volume: 10.0 µl; Temperature: 35° C.; Run time: 20 min; Mobile phase: A=$CH_3CN$, B=aq. 10 mmol $KH_2PO_4$, pH=3 ($H_3PO_4$); Flow: 1.00 ml/min; Gradient: 0 min=1.0% A+99.0% B, 10.00 min =60.0% A+40.0% B, 15.00 min=85.0% A+15.0% B, 16.00 min=85.0% A+15.0% B, 16.01 min=1.0% A+99.0% B. The reaction was considered complete when <1% (HPLC AP) of intermediate 4 remained (approximate retention time of 4 was 6.93 min).

Stage 2B, Synthesis of Crude Compound I, In-Process: A sample of the reaction mixture (0.1 ml) was diluted with 10 ml of 1:1 $CH_3CN$:0.1% aq. $H_3PO_4$ and then analyzed using the following HPLC conditions. Column: Phenomenex HYPERSIL™ BDS C8 (4.6×250 mm), 5µ, 120 A; Detection: 210, 240 nm, UV detector; Injection volume: 10.0 µl; Temperature: 35° C.; Run time: 20 min; Mobile phase: 20:80 $CH_3CN$: aq. 10 mmol $KH_2PO_4$, pH=3 ($H_3PO_4$); Flow: 1.00 ml/min. The reaction was considered complete when <1% (HPLC AP) of intermediate 6 remained (approximate retention time of 6 was 15.4 min).

Crude or Recrystallized Compound I, Purity: 50 mg of Crude Compound I was dissolved and diluted with 100 ml of 1:1 $CH_3CN$:0.1% aq. $H_3PO_4$ and then analyzed using the following HPLC conditions. Column: Phenomenex HYPERSIL™ BDS C8 (4.6×250 mm), 5µ, 120 A; Detection: 210, 240 nm, UV detector; Injection volume: 10.0 µl; Temperature: 35° C.; Run time: 20 min; Mobile phase: A=$CH_3CN$, B=aq. 10 mmol $KH_2PO_4$, pH=3 ($H_3PO_4$); Flow: 1.00 ml/min; Gradient: 0 min=1.0% A+99.0% B, 10.00 min=60.0% A+40.0% B, 15.00 min=85.0% A+15.0% B, 16.00 min=85.0% A+15.0% B, 16.01 min=1.0% A+99.0% B. The approximate retention time of Compound I was 10.0 min.

All publications and patent applications cited in this specification are herein incorporated by reference as if each individual publication or patent application were specifically and individually indicated to be incorporated by reference. Although the foregoing embodiments have been described in some detail by way of illustration and example for purposes of clarity of understanding, it will be readily apparent to those of ordinary skill in the art in light of the teachings provided herein that certain changes and modifications may be made thereto without departing from the spirit or scope of the appended claims.

What is claimed is:

1. A crystal form comprising a hydrate of the compound of the formula:

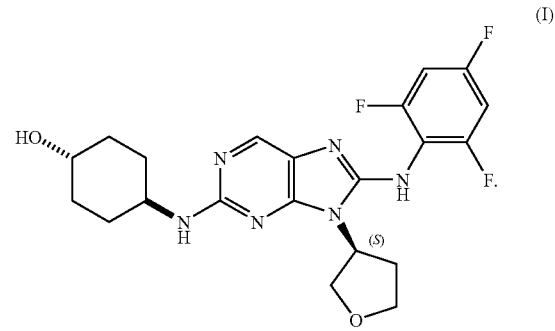

2. The crystal form of claim 1 which has an X-ray powder diffraction pattern comprising peaks at 6.5, 13.0, 23.0 and 23.8 °2θ±0.1 when measured using Cu Kα radiation.

3. The crystal form of claim 1 which comprises about 2.0 molar equivalents of water per mole of the compound in the crystal lattice.

4. A pharmaceutical composition comprising a crystal form of claim 1 and a pharmaceutically acceptable diluent, excipient or carrier.

* * * * *